United States Patent
Walt

(10) Patent No.: US 9,050,262 B2
(45) Date of Patent: Jun. 9, 2015

(54) COMPOSITIONS FOR ENHANCING NAIL HEALTH

(71) Applicant: Allergan, Inc., Irvine, CA (US)

(72) Inventor: John G. Walt, Huntington Beach, CA (US)

(73) Assignee: Allergan, Inc., Irvine, CA (US)

( * ) Notice: Subject to any disclaimer, the term of this patent is extended or adjusted under 35 U.S.C. 154(b) by 0 days.

(21) Appl. No.: 14/089,412

(22) Filed: Nov. 25, 2013

(65) Prior Publication Data

US 2014/0079655 A1 Mar. 20, 2014

Related U.S. Application Data

(63) Continuation of application No. 13/630,837, filed on Sep. 28, 2012, now abandoned.

(60) Provisional application No. 61/543,736, filed on Oct. 5, 2011.

(51) Int. Cl.

| A61K 8/42 | (2006.01) |
|---|---|
| A61K 8/64 | (2006.01) |
| A61Q 3/00 | (2006.01) |
| A61K 8/49 | (2006.01) |
| A61K 38/13 | (2006.01) |
| A61K 31/5575 | (2006.01) |
| A61K 31/407 | (2006.01) |
| A61K 8/36 | (2006.01) |
| A61K 8/06 | (2006.01) |
| A61K 9/107 | (2006.01) |
| A61K 45/06 | (2006.01) |

(52) U.S. Cl.
CPC . *A61K 8/42* (2013.01); *A61K 38/13* (2013.01); *A61Q 3/00* (2013.01); *A61K 31/5575* (2013.01); *A61K 31/407* (2013.01); *A61K 8/361* (2013.01); *A61K 8/062* (2013.01); *A61K 9/107* (2013.01); *A61K 8/492* (2013.01); *A61K 8/64* (2013.01); *A61K 45/06* (2013.01)

(58) Field of Classification Search
None
See application file for complete search history.

(56) References Cited

U.S. PATENT DOCUMENTS

| 4,254,145 A * | 3/1981 | Birnbaum .................... 514/530 |
| 4,388,307 A | 6/1983 | Cavanak |
| 5,474,979 A * | 12/1995 | Ding et al. .................... 514/20.5 |
| 6,007,798 A * | 12/1999 | Bohn et al. ..................... 424/61 |
| 6,187,745 B1 | 2/2001 | Striker et al. |
| 6,254,860 B1 | 7/2001 | Garst |
| 6,350,442 B2 | 2/2002 | Garst |
| 6,395,787 B1 | 5/2002 | Woodward et al. |
| 7,368,122 B1 | 5/2008 | Dow et al. |
| 7,368,436 B2 | 5/2008 | Gleave et al. |
| 7,550,508 B2 | 6/2009 | Lipkin et al. |
| 7,645,457 B2 | 1/2010 | Sasaki et al. |
| 2008/0275118 A1 | 11/2008 | Shaw et al. |
| 2009/0215888 A1* | 8/2009 | Jagat et al. .................... 514/479 |

FOREIGN PATENT DOCUMENTS

| WO | WO2007-042262 | 4/2007 |
| WO | 2010-080913 | 7/2010 |
| WO | WO 2010/080913 | * 7/2010 |
| WO | 2012-0112836 | 8/2012 |

OTHER PUBLICATIONS

Ogundele et al. Clinical Ophthamology vol. 4, pp. 649-652; available online from Jul. 30, 2010.*
Jia et al. Nature Rev Drug Discov, vol. 8, pp. 111-129; publication date: Feb. 2009.*
Adam S. Geyer, MD et al., Modulation of Linear Nail Growth to Treat Diseases of the Nail, Therapy, Feb. 2014, pp. 229-234, vol. 50, No. 2, American Academy of Dermatology, Inc., New York, NY.
Cohen, Joel, Enhancing the Growth of Natural Eyelashes: The Mechanism of Bimatoprost-Induced Eyelash Growth, Dermatol Surg, 2010, 1361-1371, 36(9).
Law, Simon, Bimatoprost in the Treatment of Eyelash Hypotrichosis, Clinical Ophthalmology, 2010, 349-358, 4.
Ogundele, Abayomi et al, In Vivo Comparative Study of Ocular Vasodilation, a Relative Indicator of Hyperemia, in Guinea Pigs Following Treatment With Bimatoprost Ophthalmic Solutions 0.01% and 0.03%, Clinical Ophthalmology, Jun. 19, 2010, 649-652, 4.
Patent Cooperation Treaty, Notification of Transmittal of the International Search Report and the Written Opinion of the International Searching Authority, or the Declaration, Form PCT/ISA/220, Intl. App. No. PCT/IS2012/058007, Oct. 18, 2013.
Richard Scher, MD et al., Nails:Therapy-Diagnosis-Surgery, The Nail in Older Individuals, 1997, pp. 127-150, 2nd Edition, W.B. Saunders Company.
Scher, Richard et al, Brittle Nails, Seminars in Dermatology, 1991, 21-25, 10(1).
Yoelin, Steve et al, Safety, Effectiveness, and Subjective Experience with Topical Bimatoprost 0.03% for Eyelash Growth, Dermatol. Surg., 2010, 638-649, 36.

* cited by examiner

*Primary Examiner* — Richard Schnizer
*Assistant Examiner* — Katherine Peebles
(74) *Attorney, Agent, or Firm* — Lorenz Siddiqi; Debra D. Condino

(57) ABSTRACT

The present invention is directed to compositions and methods for enhancing the health of nails and cuticles in a mammal, including humans. The compositions may be administered topically to the nail bed, nail matrix and cuticle in an amount effective to enhance nail health. The composition is also effective in strengthening and growing nails.

13 Claims, No Drawings

COMPOSITIONS FOR ENHANCING NAIL HEALTH

CROSS REFERENCE TO RELATED APPLICATIONS

This application is a continuation of U.S. Ser. No. 13/630,837, filed Sep. 28, 2012, which claims the benefit of U.S. Provisional Ser. No. 61/543,736, filed Oct. 5, 2011, which is incorporated by reference herein in its entirety.

FIELD OF THE INVENTION

The present application is directed to compositions for enhancing nail and cuticle health and growth.

BACKGROUND OF THE INVENTION

Hair and nails, including toenails and fingernails, are primarily composed of the protein keratin. These protein amino acid chains are held together by similar peptide bonds. The factors that affect the growth of nails and hair and the requirements for their proper health are similar.

Fingernails and toenails are living tissue. The nail is formed in a pocket of skin which has grown inward and is called the nail matrix. This area generates the nail and is also called the root of the nail. The outer layer of the matrix contains specialized cells that create the keratin that grows out as the nail plate. The nail plate is the commonly referred to as a fingernail or toenail.

The nail bed is the finger tissue or toe tissue that supports the nail. Nails grow continuously throughout a person's life, growing approximately at an average rate of 3 millimeters a month. Fingernails may require 3 to 6 months to re-grow completely, and toenails require approximately 12 to 18 months. Actual growth rate is dependent upon age, gender, season, exercise level, diet, and hereditary factors.

Poor nail and cuticle health can result in Brittle Nail Syndrome. Brittle Nail Syndrome can be characterized by trachyonychia (e.g. surface roughness), lamellar onychoschizia (e.g. horizontal layering/peeling), and/or onychorrhexis (e.g. longitudinal cracking or splitting of the distal edge). In addition, Brittle Nail Syndrome can also result in nail fragility, lack of thickness and/or poor nail growth. Brittle Nail Syndrome is due in part to chronic inflammation of the nail bed.

The treatment of fingernail and toe nail problems due to various conditions such as anemia, vitamin or mineral deficiency, onychorrhexis, kidney and liver disorders, psoriasis, vascular disease (e.g., Raynaud's disease) and heart disease often result in poor nail growth, vertical trenches, pitting, cracking, horizontal lines, lack of thickness and strength, lack of smoothness, tendency to tear and other symptoms of Brittle Nail Syndrome.

Despite the development of numerous treatments such as the use of nail enhancement and hardening polishes, protein elixirs such as bovine collagen emulsions, various types of wearable protective fingernail covers and other similar products, there remains a significant need for treatments which actually restore the health of nails and cuticles. The problem with current treatments for improving nail health is that they are mainly cosmetic in nature, largely ineffective, are generally taken systemically (e.g., biotin and silicon) and time consuming. There is a need for compositions which actually restore nails and cuticles to their natural health.

It is therefore an object of the present invention to provide a novel and effective treatment for brittle nail syndrome and/or the enhancement of nail health and cuticle health.

DESCRIPTION

The present invention is directed to compositions and methods for enhancing nail health, cuticle health and/or nail growth in a mammal, including humans. Certain embodiments of the invention are directed to compositions and methods for treating Brittle Nail Syndrome in a mammal, including humans. In certain embodiments the compositions include one or more prostaglandins and/or prostamides, including analogs/prodrugs thereof. In certain other embodiments the compositions include one or more anti-inflammatory drugs. In further embodiments the compositions include one or more prostaglandins and/or prostamides in combination with one or more anti-inflammatory drugs.

In certain embodiments of the present invention the composition used for enhancing nail health comprises bimatoprost. Bimatoprost, is sold by Allergan, Inc. of Irvine, Calif., U.S.A. as Lumigan® ophthalmic solution, for treating glaucoma, and as Latisse® for increasing the growth of eyelashes when applied in the FDA approved manner.

The compositions can be administered topically to the nail bed, nail matrix, the end or tip of the nail and cuticle in an amount effective to enhance nail health and/or cuticle health, for example by thickening, strengthening and/or smoothing the nail and/or cuticle, and in certain embodiments by treating Brittle Nail Syndrome. In certain embodiments the compositions can be administered topically to the nail bed, nail matrix, the end or tip of the nail and cuticle in an amount effective to enhance nail growth. The composition can be administered once a day, twice a day, three times a day, four times a day, five times a day, six times a day, once a week, twice a week, three times a week, four times a week, five times a week or six times a week. The composition can come in a kit comprising a vial or dispenser containing the composition and an applicator (e.g. brush).

The compositions of the present invention include but are not limited to emulsions, microemulsions, reverse emulsions, solutions, colloids, suspensions, dispersions, gels, pastes and polishes. In certain embodiments the composition includes at least one active compound selected from a prostaglandin, a prostamide, and analogs/prodrugs/derivatives thereof. In at least one embodiment the composition includes at least one prostamide derivative (e.g. bimatoprost). In at least one embodiment the composition includes a combination of a prostamide derivative (e.g. bimatoprost) and an anti-inflammatory (e.g. ketorolac). In other embodiments the composition includes a combination of at least one prostamide derivative and at least one immunomodulator. In at least one embodiment the composition includes a combination of bimatoprost and cyclosporine. In other embodiments the composition includes at least one retinoid such as tazarotene. In certain embodiments the composition includes biotin and/or silicone.

Certain embodiments of the present invention are directed to oil-in-water emulsions optionally containing an active compound wherein the emulsions can contain at least one oil and/or surfactant. In one embodiment the emulsion contains castor oil, polysorbate 80, glycerine, NaOH and may optionally contain polyacrylates such as carbomer and PEMULEN® and other additional ingredients.

In at least one embodiment of the present invention the composition includes 0.5% w/v carboxymethyl cellulose, 0.9% w/v glycerine, 0.25% carnitine and 0.25% w/v erythritol and purite.

Castor oil or another oil or another hydrophobic component, such as vegetable oils, animal oils, mineral oils, synthetic oils, higher fatty acid glycerides and the like and mixtures thereof, some of which are listed below in the Detailed Description, may be present in the composition in concentrations from 1.25% w/v, 0.01%-w/v-10.0% w/v, 0.1% w/v-5.0% w/v, 0.1% w/v-4.0% w/v, 0.1% w/v-3.0% w/v, 0.1% w/v-2.0% w/v, 0.1% w/v-1.0% w/v, 0.1% w/v-0.9% w/v, 0.1% w/v-0.8% w/v, 0.1% w/v-0.8% w/v, 0.1% w/v-0.7% w/v, 0.1% w/v-0.6% w/v, 0.1% w/v-0.5% w/v, 0.1% w/v-0.4% w/v, 0.1% w/v-0.3% w/v, 0.1% w/v-0.2% w/v, 0.09%-0.1% w/v, 0.08%-0.1% w/v, 0.07%-0.1% w/v, 0.06%-0.1% w/v, 0.05%-0.1% w/v, 0.04%-0.1% w/v, 0.03%-0.1% w/v, 0.02%-0.1% w/v, 0.01%-0.1% w/v, 0.01-0.09%, 0.01-0.08% 0.01-0.07% w/v, 0.01-0.06% w/v, 0.01-0.05% w/v, 0.01-0.04% w/v, 0.01-0.03% w/v, 0.01-0.02% w/v, 0.01-0.0125% w/v and most preferably 0.05% w/v-5.0% w/w.

Polysorbate 80 or another suitable surfactant, such as alcohols including carboxylated and ethoxylated alcohols, amine oxides, block polymers, fatty acids including carboxylic fatty acids, ethoxylated alkyl phenols, ethoxylated fatty esters, glycerol esters, lanolin-based derivatives, lignin derivatives, methyl esters, mono- and tri-glycerides, polyethylene glycols, polymeric surfactants, propoxylated and ethoxylated fatty acids, alcohols, or alkyl phenols, protein based surfactants, sucrose and glucose esters and derivatives, some of which are listed below in the Detailed Description, may be present in concentrations of in certain embodiments in the amount of 1.0% w/v or 0.01%-w/v-10.0% w/v, 0.1% w/v-5.0% w/v, 0.1% w/v-4.0% w/v, 0.1% w/v-3.0% w/v, 0.1% w/v-2.0% w/v, 0.1% w/v-1.0% w/v, 0.1% w/v-0.9% w/v, 0.1% w/v-0.8% w/v, 0.1% w/v-0.7% w/v, 0.1% w/v-0.6% w/v, 0.1% w/v-0.5% w/v, 0.1% w/v-0.4% w/v, 0.1% w/v-0.3% w/v, 0.1% w/v-0.2% w/v, 0.09%-0.1% w/v, 0.08%-0.1% w/v, 0.07%-0.1% w/v, 0.06%-0.1% w/v, 0.05%-0.1% w/v, 0.04%-0.1% w/v, 0.03%-0.1% w/v, 0.02%-0.1% w/v, 0.01%-0.1% w/v, 0.01-0.09%, 0.01-0.08% 0.01-0.07% w/v, 0.01-0.06% w/v, 0.01-0.05% w/v, 0.01-0.04% w/v, 0.01-0.03% w/v, 0.01-0.02% w/v and 0.01-0.0125% w/v.

Pemulen TR-2 or carbomer 1342, or other polymers or polymers of acrylic acid which are well known in the art can be present in the amounts of 0.05% w/w or 0.01%-w/v-10.0% w/v, 0.1% w/v-5.0% w/v, 0.1% w/v-4.0% w/v, 0.1% w/v-3.0% w/v, 0.1% w/v-2.0% w/v, 0.1% w/v-1.0% w/v, 0.1% w/v-0.9% w/v, 0.1% w/v-0.8% w/v, 0.1% w/v-0.7% w/v, 0.1% w/v-0.6% w/v, 0.1% w/v-0.5% w/v, 0.1% w/v-0.4% w/v, 0.1% w/v-0.3% w/v, 0.1% w/v-0.2% w/v, 0.09%-0.1% w/v, 0.08%-0.1% w/v, 0.07%-0.1% w/v, 0.06%-0.1% w/v, 0.05%-0.1% w/v, 0.04%-0.1% w/v, 0.03%-0.1% w/v, 0.02%-0.1% w/v, 0.01%-0.1% w/v, 0.01-0.09%, 0.01-0.08% 0.01-0.07% w/v, 0.01-0.06% w/v, 0.01-0.05% w/v, 0.01-0.04% w/v, 0.01-0.03% w/v, 0.01-0.02% w/v and 0.01-0.0125% w/v.

Glycerine and mannitol, or other tonicity adjusters which are known in the art, can be present in the amounts of 1.0% w/w or 2.0% w/w respectively, or 0.01%-w/v-10.0% w/v, 0.1% w/v-5.0% w/v, 0.1% w/v-4.0% w/v, 0.1% w/v-3.0% w/v, 0.1% w/v-2.0% w/v, 0.1% w/v-1.0% w/v, 0.1% w/v-0.9% w/v, 0.1% w/v-0.8% w/v, 0.1% w/v-0.7% w/v, 0.1% w/v-0.6% w/v, 0.1% w/v-0.5% w/v, 0.1% w/v-0.4% w/v, 0.1% w/v-0.3% w/v, 0.1% w/v-0.2% w/v, 0.09%-0.1% w/v, 0.08%-0.1% w/v, 0.07%-0.1% w/v, 0.06%-0.1% w/v, 0.05%-0.1% w/v, 0.04%-0.1% w/v, 0.03%-0.1% w/v, 0.02%-0.1% w/v, 0.01%-0.1% w/v, 0.01-0.09%, 0.01-0.08% 0.01-0.07% w/v, 0.01-0.06% w/v, 0.01-0.05% w/v, 0.01-0.04% w/v, 0.01-0.03% w/v, 0.01-0.02% w/v and 0.01-0.0125% w/v.

In one embodiment, the emulsion contains: 1.0% w/w polysorbate 80, 0.05% w/w glycerine, 1.0% w/w castor oil, 0.08% w/w pemulen TR-2, 1.5% w/w mannitol, sodium hydroxide to a pH of 7.4 and purified water. Another embodiment includes an emulsion that contains: 1.0% w/w polysorbate 80, 1.0% w/w glycerine, 1.25% w/w castor oil, 0.05% w/w pemulen TR-2, 2.0% w/w mannitol, sodium hydroxide to a pH of 7.4 and purified water. Another emulsion contains: 1.5% w/w polysorbate 80, 0.05% w/w glycerine, 0.05% w/w castor oil, 0.08% w/w pemulen TR-2, 1.5% w/w mannitol, sodium hydroxide to a pH of 7.4 and purified water. Another emulsion of the present invention contains 1.2% w/w polysorbate 80, 1.0% w/w glycerine, 1.50% w/w castor oil, 0.05% w/w pemulen TR-2, 2.5% w/w mannitol, sodium hydroxide to a pH of 7.4 and purified water. Another emulsion of the present invention 0.5% w/w polysorbate 80, 1.0% w/w glycerine, 1.25% w/w castor oil, 0.05% w/w pemulen TR-2, 1.0% w/w mannitol, sodium hydroxide to a pH of 7.4 and purified water.

Certain embodiments of the invention include:

1. A composition for use in enhancing nail health, enhancing cuticle health, and/or enhancing nail growth in a human or animal, the composition comprising at least one of a prostaglandin, prostamide, and analog/prodrug/derivative thereof and mixture thereof.

2. The composition of embodiment 1, wherein the composition is an oil-in-water emulsion.

3. The composition of embodiment 2, wherein the emulsion comprises castor oil and a surfactant.

4. The composition of embodiment 2 or 3, wherein the emulsion further comprises an anti-inflammatory drug and/or an immunomodulator.

5. The composition of embodiment 4, wherein the anti-inflammatory is ketorolac.

6. The composition of embodiment 4, wherein the immunomodulator is cyclosporine A.

7. The composition of any of embodiment 2-6, wherein the emulsion comprises bimatoprost.

8. The composition of any of embodiments 2-7, wherein the emulsion further comprises at least one component selected from the group consisting of glycerin, polysorbate 80 and carbomer.

9. The composition of embodiment 8, wherein said carbomer is carbomer 1342.

10. The composition of any of embodiments 1-9, comprising 1.0% w/v polysorbate 80, 2.2% w/v glycerine, 1.25% w/v castor oil, 0.05% w/v pemulen.

11. The composition of any of embodiments 1-9, comprising 0.5%-1.5% w/w polysorbate 80, 0.5%-1.5% w/w glycerine, 0.5%-1.5% w/w castor oil, 0.05%-0.1% w/w carbomer 1342 and mannitol.

12. The composition of any of embodiments 1-12, which is also useful for treating a disorder of the toenail or fingernail selected from the group consisting of Brittle Nail Syndrome, nail psoriasis, psoriatic nail dystrophy, brittle nail syndrome, increasing nail length and thickness, onychia, onychogryphosis, onychatrophia, onychocryptosis, onychodystrophy, onychogryposis, onycholysis, onychomadesis, onychauxis, onychomycosis, onychorrhexis, tinea unguium, onychophosis, onychoptosis, paronychia, pseudomonas, pterygium and pterygium inversum unguis, koilonychia, subungual hematoma or other trauma to the nail, folic acid deficiency, leukonychia, nail patella syndrome, melanonychia, protein deficiency, brittle and peeling nails, methyl methacrylate damaged nails, vitamin C deficiency, vitamin deficiency, tinea unguis, thinning nails associated with lichen planus, Raynaud's disease, bleeding associated with rheumatoid arthritis, beau's lines, and Mee's lines associated with certain kinds of poisoning.

13. A method of enhancing nail health, enhancing cuticle health and/or enhancing nail growth in a human or animal, the method comprising:

topically applying an oil-in-water emulsion to the nails, cuticles or nail matrix of the human or animal at least once a day, wherein the emulsion comprises at least one of a prostaglandin, prostamide, and analog/prodrug/derivative thereof.

14. The method of embodiment 13, wherein the oil-in-water emulsion further comprises an anti-inflammatory drug and/or an immunomodulator.

15. The method of any of embodiments 13 or 14, wherein the oil-in-water emulsion comprises bimatoprost.

16. The method of any of embodiments 13-15, wherein the oil is castor oil and further including the surfactant polysorbate 80.

17. The method of any of embodiments 13-16, further comprising glycerine.

18. The method of any of embodiments 13-15, wherein the oil is selected from the group consisting of: Anise oil; Castor oil; Clove oil; Cassia oil; Cinnamon oil; oils having a specific gravity between 0.90 and 0.95; Almond oil; Corn oil; Arachis oil; Cottonseed oil; Safflower oil; Maize oil; Linseed oil; Rapeseed oil; Soybean oil; Olive oil; Caraway oil; Rosemary oil; Peanut oil; Peppermint oil; Sunflower oil; Eucalyptus oil; Sesame oil; an oil having a specific gravity below 0.9; Mineral oil; Coriander oil; Lavender oil; Citronella oil; Juniper oil; Lemon oil; Orange oil; Clary sage oil; Nutmeg oil; and, Tea tree oil.

19. The method of any of embodiments 13-15, wherein the oil-in-water emulsion further contains a surfactant selected from the group consisting of Polysorbate 80, carboxylated and ethoxylated alcohols, amine oxides, block polymers, fatty acids including carboxylic fatty acids, ethoxylated alkyl phenols, ethoxylated fatty esters, glycerol esters, lanolin-based derivatives, lignin derivatives, methyl esters, mono- and tri-glycerides, polyethylene glycols, polymeric surfactants, propoxylated and ethoxylated fatty acids, alcohols, or alkyl phenols, protein based surfactants, sucrose and glucose esters and derivatives.

20. The method of any of embodiments 13-15, 18, and 19, wherein the oil is present in a concentration selected from the group consisting of 0.01%-w/v-10.0% w/v, 0.1% w/v-5.0% w/v, 0.1% w/v-4.0% w/v, 0.1% w/v-3.0% w/v, 0.1% w/v-2.0% w/v, 0.1% w/v-1.0% w/v, 0.1% w/v-0.9% w/v, 0.1% w/v-0.8% w/v, 0.1% w/v-0.8% w/v, 0.1% w/v-0.7% w/v, 0.1% w/v-0.6% w/v, 0.1% w/v-0.5% w/v, 0.1% w/v-0.4% w/v, 0.1% w/v-0.3% w/v, 0.1% w/v-0.2% w/v, 0.09%-0.1% w/v, 0.08%-0.1% w/v, 0.07%-0.1% w/v, 0.06%-0.1% w/v, 0.05%-0.1% w/v, 0.04%-0.1% w/v, 0.03%-0.1% w/v, 0.02%-0.1% w/v, 0.01%-0.1% w/v, 0.01-0.09%, 0.01-0.08% 0.01-0.07% w/v, 0.01-0.06% w/v, 0.01-0.05% w/v, 0.01-0.04% w/v, 0.01-0.03% w/v, 0.01-0.02% w/v, 0.01-0.0125% w/v and most preferably 0.05% w/v-5.0% w/v.

21. The method of any of embodiments 13-15, 18, 19, and 20, wherein the surfactant is present in a concentration selected from the group consisting of 1.0% w/v, 0.01%-w/v-10.0% w/v, 0.1% w/v-5.0% w/v, 0.1% w/v-4.0% w/v, 0.1% w/v-3.0% w/v, 0.1% w/v-2.0% w/v, 0.1% w/v-1.0% w/v, 0.1% w/v-0.9% w/v, 0.1% w/v-0.8% w/v, 0.1% w/v-0.7% w/v, 0.1% w/v-0.6% w/v, 0.1% w/v-0.5% w/v, 0.1% w/v-0.4% w/v, 0.1% w/v-0.3% w/v, 0.1% w/v-0.2% w/v, 0.09%-0.1% w/v, 0.08%-0.1% w/v, 0.07%-0.1% w/v, 0.06%-0.1% w/v, 0.05%-0.1% w/v, 0.04%-0.1% w/v, 0.03%-0.1% w/v, 0.02%-0.1% w/v, 0.01%-0.1% w/v, 0.01-0.09%, 0.01-0.08% 0.01-0.07% w/v, 0.01-0.06% w/v, 0.01-0.05% w/v, 0.01-0.04% w/v, 0.01-0.03% w/v, 0.01-0.02% w/v and 0.01-0.0125% w/v.

22. The method of any of embodiments 1-21, which is also useful for treating a disorder of the toenail and fingernail selected from the group consisting of Brittle Nail Syndrome, nail psoriasis, psoriatic nail dystrophy, brittle nail syndrome, increasing nail length and thickness, onychia, onychogryphosis, onychatrophia, onychocryptosis, onychodystrophy, onychogryposis, onycholysis, onychomadesis, onychauxis, onychomycosis, onychorrhexis, tinea unguium, onychophosis, onychoptosis, paronychia, pseudomonas, pterygium and pterygium inversum unguis, koilonychia, subungual hematoma or other trauma to the nail, folic acid deficiency, leukonychia, nail patella syndrome, melanonychia, protein deficiency, brittle and peeling nails, methyl methacrylate damaged nails, vitamin C deficiency, vitamin deficiency, tinea unguis, thinning nails associated with lichen planus, Raynaud's disease, bleeding associated with rheumatoid arthritis, beau's lines, and Mee's lines associated with certain kinds of poisoning.

23. Use of a pharmaceutical or cosmetic composition for the manufacture of a medicament for the treatment of a disease selected from the group consisting of Brittle Nail Syndrome, nail psoriasis, psoriatic nail dystrophy, onychia, onychogryphosis, onychatrophia, onychocryptosis, onychodystrophy, onychogryposis, onycholysis, onychomadesis, onychauxis, onychomycosis, onychorrhexis, tinea unguium, onychophosis, onychoptosis, paronychia, pseudomonas, pterygium and pterygium inversum unguis, koilonychia, subungual hematoma or other trauma to the nail, folic acid deficiency, leukonychia, nail patella syndrome, melanonychia, protein deficiency, brittle and peeling nails, methyl methacrylate damaged nails, vitamin C deficiency, vitamin deficiency, tinea unguis, thinning nails associated with lichen planus, Raynaud's disease, bleeding associated with rheumatoid arthritis, beau's lines, and Mee's lines wherein the composition is an oil-in-water emulsion, and comprises an immunomodulator and/or an anti-inflammatory.

24. The use of embodiment 22, wherein bimatoprost is present in a concentration selected from the group consisting of 0.1 to 20% w/v, 0.1-10% w/v, 0.1-5% w/v, 0.1-1.0% w/v, 0.09%-0.1% w/v, 0.08%-0.1% w/v, 0.07%-0.1% w/v, 0.06%-0.1% w/v, 0.05%-0.1% w/v, 0.04%-0.1% w/v, 0.03%-0.1% w/v, 0.02%-0.1% w/v, 0.01%-0.1% w/v, 0.01-0.09%, 0.01-0.08% 0.01-0.07% w/v, 0.01-0.06% w/v, 0.01-0.05% w/v, 0.01-0.04% w/v, 0.01-0.03% w/v, 0.01-0.02% w/v, 0.01-0.0125% w/v and most preferably 0.01 to 0.05% or 0.01% w/v, 0.0125% w/v, 0.02% w/v, 0.03% w/v, 0.04% w/v, 0.05% w/v, 0.06% w/v, 0.07% w/v, 0.08% w/v, 0.09% w/v, 0.1% w/v, 0.005% w/v and 0.0015% w/v.

DETAILED DESCRIPTION

Definitions

As used herein, the following definitions apply:

"Brittle Nail Syndrome" means brittleness, fragility, hangnails, peeling, cracking, raggedness, dullness, thinning, layering, roughness, and/or fraying of the nail.

"Cuticle" or "eponychium" means the thickened layer of skin surrounding the nail.

"Enhancing nail growth" means an increase in nail growth rate and/or nail thickness.

"Enhancing nail health" or "improving nail health" means a decrease in nail pitting, nail cracking, nail splitting, nail dullness, nail roughness, (trachyonychia) nail raggedness, nail peeling, nail fraying, tendency to tear, nail layering (lamellar onychoschizia), Beau's lines, onychomadesis, onycholysis, onychorrhexis, nail fragility, nail paronychia, nail onychomycosis, and/or Brittle Nail Syndrome. "Enhancing nail health" includes the treatment of Brittle Nail Syndrome.

"Excipients" means any material that is combined with a drug (e.g. "immunomodulator" and/or "anti-inflammatory") in order to produce a drug dosage form. Such Excipients can be combined, for example, to facilitate drug delivery. Non-limiting examples of excipients include, for example, water, oils, surfactants and colorants.

"Nail" means toenail and/or fingernail. Nail includes the nail plate, the nail matrix, the nail bed below it, and the nail grooves surrounding it. Nails are made of keratin.

"Safe and effective amount" means an amount of the composition which is sufficient to provide a level of treatment to a condition, but is not so great as to provide side effects to the user that are so great as to make treatment medically imprudent.

"Therapeutically effective" or "treatment" in context of a formulation means that when applied to the nail according to sound medical practice, it causes a demonstrable effect to enhance nail health, enhance cuticle health, and/or enhance nail growth. Such demonstration can be at the gross pathological level (e.g. visual improvement of nail health by, for example, reduction in brittleness, peeling, cracking, raggedness, roughness and/or hangnails; and/or measurable increase in nail growth), or subjective level (subject's perception of enhanced nail health, cuticle health and/or nail growth). Therapeutically effective or Treatment can be curative, palliative and/or prophylactic or preventive treatment.

"%", in reference to a concentration of a component of a composition, means the ratio of weight of a component to total weight expressed as a percent, unless otherwise stated.

Useful compositions for practicing the invention can be emulsions, colloids, suspensions, semi-solids, solutions, dispersions, capsules, gels, lotions, creams and the like. Compositions of the present invention include at least one of a prostaglandin, prostamide, and/or an analog prodrug or derivative thereof (e.g. bimatoprost), an anti-inflammatory (e.g. ketorolac), an immunomodulator (e.g. cyclosporine), retinoid (e.g. tazarotene), biotin, and silicone. In certain embodiments prostaglandin and/or prostamide components can be combined with carriers which form emulsions upon mixing with water. Emulsions are described, for example, and without limitation, in Cavanak U.S. Pat. No. 4,388,307, the disclosure of which is hereby incorporated in its entirety by reference.

The compositions of the present invention are applied topically on the nail by an applicator and in certain embodiments can be administered once or multiple times-a-day. In accordance with the present invention, the emulsion formulations work to enhance nail health, enhance cuticle health, and/or enhance nail growth. For example, in certain embodiments the emulsion formulations work to improve and/or restore nails and cuticles to their natural health (e.g. to thicken, strengthen and smooth the nail), and improved nail growth in thickness and length. The compositions of the present invention may be used for treatment of disorders of the toenail and fingernail such as Brittle Nail Syndrome, nail psoriasis, psoriatic nail dystrophy, brittle nail syndrome, increasing nail length and thickness, onychia, onychogryphosis, onychatrophia, onychocryptosis, onychodystrophy, onychogryposis, onycholysis, onychomadesis, onychauxis, onychomycosis, onychorrhexis, tinea unguium, onychophosis, onychoptosis, paronychia, pseudomonas, pterygium and pterygium inversum unguis, koilonychia, subungual hematoma or other trauma to the nail, folic acid deficiency, leukonychia, nail patella syndrome, melanonychia, protein deficiency, brittle and peeling nails, methyl methacrylate damaged nails, vitamin C deficiency, vitamin deficiency, tinea unguis, thinning nails associated with lichen planus, Raynaud's disease, bleeding associated with rheumatoid arthritis, beau's lines, and Mee's lines associated with certain kinds of poisoning.

In addition these compositions will contribute to enhance global nail health, increase nail strength, increase nail growth rate and thickness, increase cuticle health, decrease brittle nail syndrome, decrease weak nails, decrease nail pitting, decrease nail cracking, decrease nail splitting, decrease nail dullness, decrease nail roughness, (trachyonychia) decrease nail raggedness, decrease nail peeling, decrease nail fraying, decrease nails tendency to tear, decrease nail layering (lamellar onychoschizia), decrease Beau's lines, decrease onychomadesis, decrease onycholysis, decrease onychorrhexis, decrease nail fragility, decrease nail paronychia, and decrease nail onychomycosis.

In alternative embodiments of the present invention such as when comprising water-in-oil emulsions, the emulsions include hydrophobic components such as a pharmaceutically acceptable oil. The hydrophobic component may be present in an effective amount, for example, in an amount of up to about 0.01%-90% w/v but preferably from about 0.01-10% by w/v, 0.05%-5% w/v, 0.05%-2% w/v or 1.0%-1.5% by w/v. Examples of useful pharmaceutically acceptable oils include vegetable oils, animal oils, mineral oils, synthetic oils and the like and mixtures thereof. In alternate embodiments, the hydrophobic component may comprise or consist of one or higher fatty acid glycerides. In certain embodiments, the hydrophobic component comprises castor oil.

Surfactants may also be present in amounts of up to about 0.01-10% by w/v, 0.05%-5% w/v, 0.05%-2% w/v or 1.0%-1.5% by w/v. Surfactants may include alcohols including carboxylated and ethoxylated alcohols, amine oxides, block polymers, fatty acids including carboxylic fatty acids, ethoxylated alkyl phenols, ethoxylated fatty esters, glycerol esters, lanolin-based derivatives, lignin derivatives, methyl esters, mono- and tri-glycerides, polyethylene glycols, polymeric surfactants, propoxylated and ethoxylated fatty acids, alcohols, or alkyl phenols, protein based surfactants, sucrose and glucose esters and derivatives, In certain embodiments, the surfactant is a polysorbate and in particular polysorbate 80, but other surfactants may be used.

Any known pharmaceutically acceptable surfactants may be used, including nonionic, anionic, cationic, and combinations thereof. Nonionic surfactants can be used, including those surfactants having a hydrophile/lipophile balance (HLB) of 10 or more. Alternatively, certain combinations of high- and low-HLB surfactants may be utilized; including such mixed surfactants used in ratio such that the aggregate surfactant HLB (when weighted according to proportions used) remains in excess of 10.

Examples of suitable surfactants include, but are not limited to, polyoxyethylene derivatives of natural or hydrogenated vegetable oils such as castor oil; polyoxyethylene-sorbitan fatty acid esters, such as mono-, di- and tri-lauryl, palmityl, stearyl and oleyl esters; alkyl/dialkyl sulfate, sulfonate or sulfosuccinate salts such as sodium lauryl sulfate and dioctyl sodium sulfosuccinate; polyoxyethylene fatty acid esters; phospholipids such as lecithins; transesterification products of natural vegetable oil triglycerides and polyalkylene polyols; sorbitan fatty acid esters; pentaerythritol fatty acid esters; polyoxyethylene glycol alkyl ethers and esters; and the like. The surfactants may be used alone or in combination.

Examples of specific surfactants which may be used include, without limitation, polyoxyethylene castor oil derivatives, such as polyoxyethylene glycerol triricinoleate polyoxyl 35 castor oil (CREMOPHOR® EL, available from BASF Corporation), and polyoxyl 40 hydrogenated castor oil (CREMOPHOR® RH40, available from BASF Corporation); mono-fatty acid esters of polyoxyethylene (20) sorbitan, such as polyoxyethylene (20) sorbitan monooleate (TWEEN® 80), polyoxyethylene (20) sorbitan monostearate (TWEEN® 60), polyoxyethylene (20) sorbitan monopalmitate (TWEEN® 40), and polyoxyethylene (20) sorbitan monolaurate (TWEEN® 20) (all available from ICI Surfactants, Wilmington, Del.); polyoxyethylene glycol 200 monostearate (MYRJ® 52, available from Calgene Chemicals, Skokie, Ill.); polyglycerol esters with a HLB of 10 or greater, such as decaglycerol mono- and dioleate and the like; and mixtures thereof.

In some instances (as when the compositions are prepared as semi-solids), it may be advantageous to use at least one additional low-HLB surfactant along with one or more of the above high-HLB surfactant. Examples of low-HLB auxiliary surfactants which may be used include, but are not limited to, polyglycerol oleates (such as CAPROL® 10G40); lecithins; glyceryl monooleate or monolinoleate mixtures (such as MYVEROL® 18-99 or 18-92); propylene glycol laurate; and sorbitan oleates such as sorbitan monooleate (SPAN® 80), sorbitan trioleate (SPAN® 85), and sorbitan sesquioleate (SPAN® 20) (all available from ICI Surfactants, Wilmington, Del.). The surfactant phase may comprise about 10% to 90% by weight of the composition. In certain embodiments the surfactant comprises about 20% to about 70% of the composition, and other embodiments about 40% to about 60%, by weight.

(I) Prostaglandins and Prostamides

Prostaglandins are a class of pharmacologically active hormone-like substances that mediate a wide range of physiological functions including blood pressure, smooth muscle contraction, inflammation and vascular permeability. A prostaglandin is any member of a group of lipid compounds that are derived enzymatically from fatty acids and have important functions in the animal body. Every prostaglandin contains 20 carbon atoms, including a 5-carbon ring. Prostaglandins are autocrine and paracrine lipid mediators that act upon platelets, endothelium, uterine and mast cells. They are synthesized in the cell from the essential fatty acids (EFAs). EFAs are known to be involved in regulating water loss through the outer layers of the skin and nails. Poor nail health and nail growth are characterized by high water loss throughout the nail, as well as inflammation of the cuticle and surrounding tissue. One example of an EFA is linoleic acid (LA). An LA derivative, gamma-linolenic acid (GLA) is known to reduce inflammation, and prostaglandins are known to regulate inflammatory mediation. The present invention recognizes that LA, GLA and prostaglandins may all play a role in nail health. One of the factors in poor nail health, brittle nail syndrome and poor nail growth may be the disruption of the conversion of LA to GLA and the consequential biological inhibition of the respective prostaglandins. In at least one embodiment of the present invention, the topical application of prostaglandins are used to enhance nail health, treat brittle nail syndrome and/or enhance nail growth.

There are nine types of prostaglandins, designated by the letters A to I, the degree of saturation of the side chain of each being designated by subscripts 1, 2, and 3. Examples of prostaglandins include, without limitation, prostaglandin $E_1$ (alprostadil), prostaglandin $E_2$ (dinoprostone), latanoprost and travoprost. Latanoprost and travoprost are actually prostaglandin prodrugs (i.e. 1-isopropyl esters of a prostaglandin) however, they are referred to as prostaglandins because they act on the prostaglandin F receptor, after being hydrolyzed to the 1-carboxylic acid.

A prostamide (also called a prostaglandin-ethanolamide) is a prostaglandin analog, which is pharmacologically unique from a prostaglandin (i.e. because prostamides act on a different cell receptor [the prostamide receptor] than do prostaglandins), and is a neutral lipid formed as a product of cyclo-oxygenase-2 ("COX-2") enzyme oxygenation of an endocannabinoid (such as anandamide). Additionally, prostamides do not hydrolyze in-situ to the 1-carboxylic acid. Examples of prostamides are bimatoprost (the synthetically made ethyl amide of 17-phenyl prostaglandin $F_{2\alpha}$) and prostamide $F_{2\alpha}$.

Examples of pharmaceutically acceptable acid addition salts of the compounds of the invention are those formed from acids which form non-toxic addition salts containing pharmaceutically acceptable anions, such as the hydrochloride, hydrobromide, hydroiodide, sulfate, or bisulfate, phosphate or acid phosphate, acetate, maleate, fumarate, oxalate, lactate, tartrate, citrate, gluconate, saccharate and p-toluene sulphonate salts.

As used herein the term "derivatives" of a prostaglandin or prostamide refer to compounds having structures sufficiently similar to the prostaglandin or prostamide so as to function in a manner substantially similar to or substantially identical to the prostaglandin or prostamide.

The prostamide component of certain embodiments of the present invention comprises a compound having the formula:

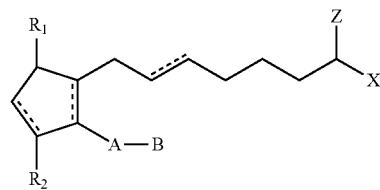

wherein the dashed bonds represent a single or double bond which can be in the cis or trans configuration, A is an alkylene or alkenylene radical having from two to six carbon atoms, which radical may be interrupted by one or more oxide radicals and substituted with one or more hydroxy, oxo, alkyloxy or alkylcarboxy groups wherein said alkyl radical comprises from one to six carbon atoms; B is a cycloalkyl radical having from three to seven carbon atoms, or an aryl radical, selected from the group consisting of hydrocarbyl aryl and heteroaryl radicals having from four to ten carbon atoms wherein the heteroatom is selected from the group consisting of nitrogen, oxygen and sulfur atoms; X is —$N(R^4)_2$ wherein $R^4$ is independently selected from the group consisting of hydrogen and lower alkyl radicals having from one to six carbon atoms, Z is =O; one of $R_1$ and $R_2$ is =O, —OH or a —$O(CO)R_6$ group, and the other one is —OH or —$O(CO)R_6$, or $R_1$ is =O and $R_2$ is H; wherein $R_6$ is a saturated or unsaturated acyclic hydrocarbon group having from 1 to about 20 carbon atoms, or —$(CH_2)mR_7$ wherein m is 0-10, and $R_2$ is cycloalkyl radical, having from three to seven carbon atoms, or a hydrocarbyl aryl or heteroaryl, as defined above; or a pharmaceutically-acceptable salt thereof or a pharmaceutically-acceptable salt thereof.

In certain embodiments the prostamide has the following formula:

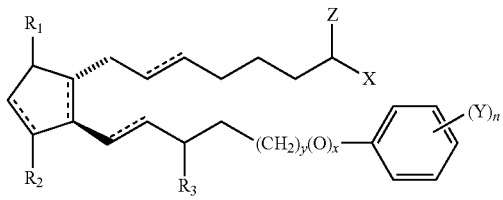

wherein y is 0 or 1, x is 0 or 1 and x+y are not both 1, Y is a radical selected from the group consisting of alkyl, halo, nitro, amino, thiol, hydroxy, alkyloxy, alkylcarboxy and halo substituted alkyl, wherein said alkyl radical comprises from one to six carbon atoms, n is 0 or an integer of from 1 to 3 and $R_3$ is =O, —OH or —O(CO)$R_6$ and hatched lines indicate the α configuration and solid triangles indicate the β configuration.

In at least one embodiment the prostamide comprises a compound wherein $R_1$, $R_2$ and $R_3$ are OH, y is 1, x is 0, n is 0 and X is N(H)($C_2H_5$), e.g. cyclopentane N-ethyl heptenamide-5-cis-2-(3α-hydroxy-5-phenyl-1-trans-pentenyl)-3, 5dihydroxy, [$1_\alpha, 2_\beta, 3_\alpha, 5_\alpha$].

The compound, cyclopentane N-ethyl heptenamide-5-cis-2-(3α-hydroxy-5-phenyl-1-transpentenyl)-3,5dihydroxy, [$1_\alpha, 2_\beta, 3_\alpha, 5_\alpha$], is also known as bimatoprost and is publicly available in a topical ophthalmic solution under the tradename, Lumigan® (Allergan, Inc., CA).

Alternatively, the prostamide may be any of the prostamides disclosed in U.S. Pat. No. 6,395,787, which is hereby incorporated by reference.

The chemical structure for bimatoprost is represented by the following formula:

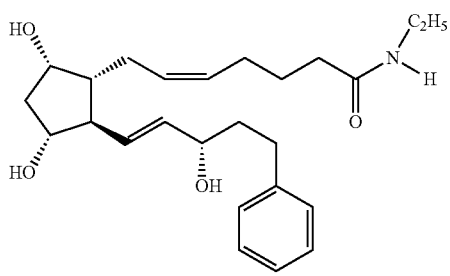 [SMILES: CCNC(=O)CCC/C=C\C[C@@H]1[C@@H](/C=C/[C@@H](O)CCc2ccccc2)[C@H](O)C[C@@H]1O]

In at least one embodiment the composition comprises bimatoprost, travoprost, latanoprost, salts thereof, analogs thereof, derivatives thereof, and/or mixtures thereof.

(II) Immunomodulators

An immunomodulator, also known as an immunotherapy is a substance (e.g. a drug) which has an effect on the immune system. Immunomodulators may be used in compositions of the present invention, and include immunosuppressants, immunostimulants and tolerogens. Immunosuppressants inhibit immune response, for example, in autoimmune diseases. Immunostimulants increase the immune response, and can be useful, for example, in infections, immunodeficiency and cancers. Tolerogens induce tolerance and make tissue non-responsive to antigen.

Immunomodulators that can be used in compositions of the present invention include and are not limited to: cyclosporine, tacrolimus, azathioprine, cyclophosphamide, methotrexate, chlorambucil, mycophenolate mofetil, prednisolone, muromonab CD3, antithymocyte globin (ATG), Rho (D) immunoglobulin, efalizumab, levamisole, thalidomide, and mixtures thereof. In at least one embodiment, the immunomodulator used in the composition is cyclosporine.

Cyclosporine

As stated previously, the compositions of the present invention may contain cyclosporine or other active compounds. Cyclosporines are a group of nonpolar cyclic oligopeptides with known immunosuppressant activity. Cyclosporine A, along with several other minor metabolites, as well as cyclosporine B, C, D, E, F, G, H, I, J, K, L, M, N, O, P, Q, R, S, T, U, V, W, X, Y and Z, have been identified. In addition, derivatives, salts and the like of such cyclosporines and a number of synthetic analogs have been prepared and may be useful in the present invention. The use of cyclosporine-A and cyclosporine A derivatives to treat ophthalmic conditions has been the subject of various patents, for example Ding et al U.S. Pat. No. 5,474,979; Garst U.S. Pat. Nos. 6,254,860; 6,350,442, and 7,368,436; the disclosure of each of which is incorporated in its entirely herein by reference.

In general, commercially available cyclosporines may contain a mixture of several individual cyclosporines which all share a cyclic peptide structure consisting of eleven amino acid residues with a total molecular weight of about 1,200, but with different substituents or configurations of some of the amino acids.

The term "cyclosporine component" as used herein is intended to include any individual member of the cyclosporine group, salts thereof, derivatives thereof, analogs thereof and mixtures thereof, as well as mixtures of two or more individual cyclosporines salts thereof, derivatives thereof, analogs thereof and mixtures thereof.

In certain embodiments, cyclosporine components include, without limitation, cyclosporine A, derivatives of cyclosporine A, salts of cyclosporine A and the like and mixtures thereof. Cyclosporine A is a useful cyclosporine component.

The chemical structure for cyclosporine A is represented by Formula I:

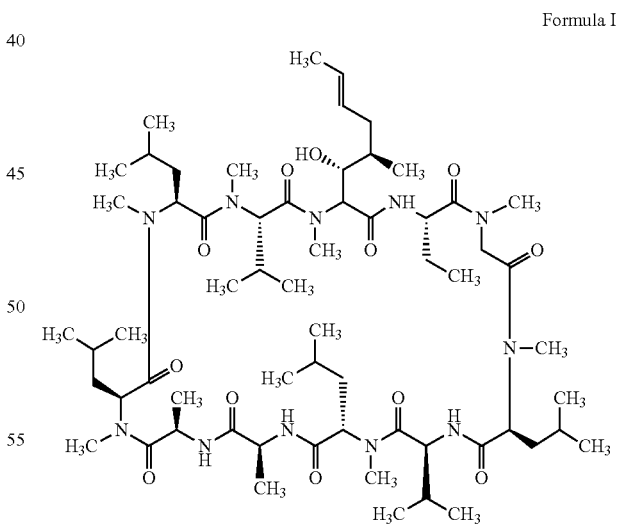

Formula I

As used herein the term "derivatives" of a cyclosporine refer to compounds having structures sufficiently similar to the cyclosporine so as to function in a manner substantially similar to or substantially identical to the cyclosporine, for example, cyclosporine A, in the present methods. Included, without limitation, within the useful cyclosporine A derivatives are those selected from ((R)-methylthio-Sar)[3]-(4'-hydroxy-MeLeu) cyclosporine A, ((R)-(Cyclo)alkylthio-Sar)[3]-

(4'-hydroxy-MeLeu)⁴-cyclosporine A, and ((R)-(Cyclo)alkylthio-Sar)³-cyclosporine A derivatives described below.
These cyclosporine derivatives are represented by the following general formulas (II), (III), and (IV) respectively:
Formula II
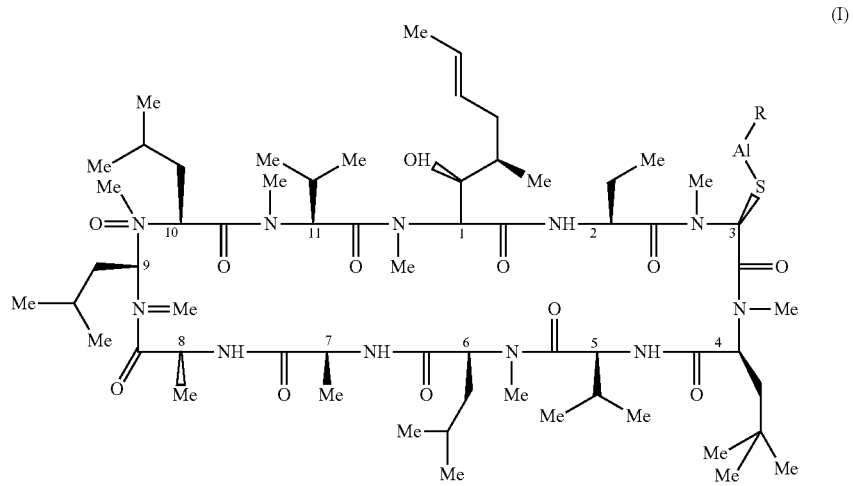
(I)
Formula III
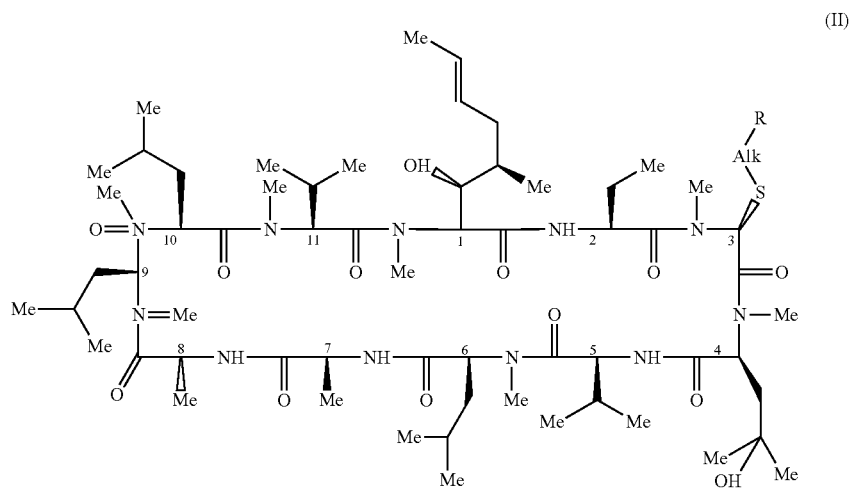
(II)
Formula IV
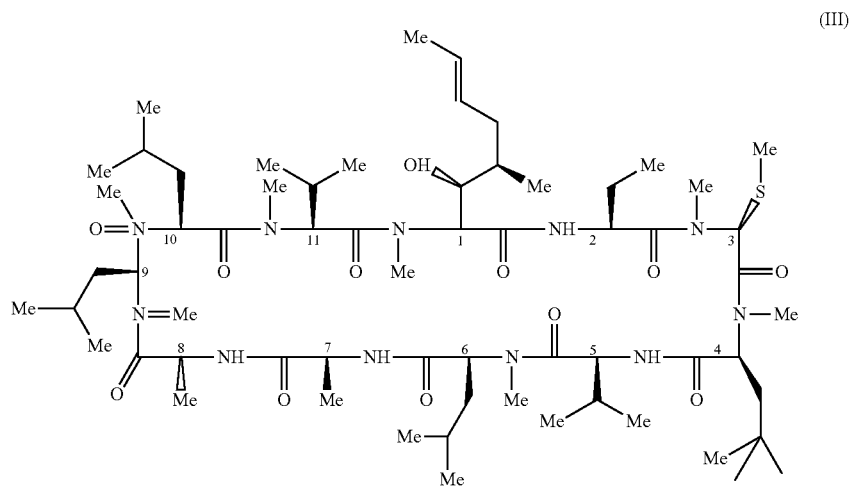
(III)

wherein Me is methyl; Alk is 2-6C alkylene or 3-6C cycloalkylene; R is OH, COOH, alkoxycarbonyl, —NR$_1$R$_2$ or N(R$_3$)—(CH$_2$)—NR$_1$R$_2$; wherein R$_1$R$_2$ is H, alkyl, 3-6C cycloalkyl, phenyl (optionally substituted by halo, alkoxy, alkoxycarbonyl, amino, alkylamino or dialkylamino), benzyl or saturated or unsaturated heterocyclyl having 5 or 6 members and 1-3 heteroatoms; or NR$_1$R$_2$ is a 5 or 6 membered heterocycle which may contain a further N, O or S heteroatom and may be alkylated; R$_3$ is H or alkyl and n is 2-4; and the alkyl moieties contain 1-4C.

(III) Anti-Inflammatory Drugs

An anti-inflammatory or anti-inflammatory drug is one or more dermatologically acceptable agents with anti-inflammatory activity which includes agents that blunt an inflammatory reaction, irrespective to the underlying mechanism (e g inhibition of prostaglandin synthesis, leukotriene production, macrophage function, etc). Anti-inflammatory drugs that can be used in the present invention include and are not limited to small molecules with elucidated structures (e.g. a nonsteroidal inflammatory drug or NSAID), and include polymorphs, crystal habits thereof, prodrugs and isomers thereof (including optical, geometric and tautomeric isomers), enantiomers, salts, solvates and complexes thereof and solvates and complexes of salts thereof.

Anti-inflammatory drugs which may be used in the compositions of the present invention include non-steroidal anti-inflammatory drugs (NSAIDs), steroids (e.g. corticosteroids), and biological or botanical extracts or preparations.

Specific examples of NSAIDs that can be used in compositions of the present invention include, without limitation, acetylsalicylic acid, alclofenac, alminoprofen, benoxaprofen, butibufen, bucloxic acid, bufexamac, carprofen, celecoxib, clidanac, diclofenac, diflunisal, entiazac, etodolac, etofenamate, felbinac, fenbufen, fenoprofen, fentiazac, fepradinol, flufenamic acid, flufenasol, flurbiprofen, furofenac, ibufenac, ibuprofen, indomethacin, indoprofen, isoxepac, isoxicam, ketoprofen, ketorolac, meclofenamic acid, mefenamic acid, meloxicam, miroprofen, naproxen, niflumic, oxaprozin, oxyphenbutazone, oxpinac, parecoxib, phenylbutazone, piclamilast, piketoprofen, piroxicam, pirprofen, pranoprofen, rofecoxib, isonixin, sudoxicam, sulindac, suprofen, suxibuzone, fenclofenac, tiaprofenic acid, tolfenamic acid, tolmetin, tramadol, valdecoxib, zomepirac, pharmacologically active basic addition salts thereof, and mixtures thereof. In at least one embodiment, the NSAID used in the composition is ketorolac.

Ketorolac

Ketorolac is a NSAID in the family of heterocyclic acetic acid derivative. Ketorolac acts by inhibiting the bodily synthesis of prostaglandins by competitive blocking of the enzyme cyclooxygenase. Ketorolac is an isostere of ketoprofen. More precisely, it is a dihydropyrrolizine carboxylic acid derivative structurally related to indomethacin. Derivatives, salts and the like of ketorolac have been prepared and may be useful in the present invention. In at least one embodiment, the tromethamine salt of ketorolac is used in a composition of the present invention. Systematic (IUPAC) name of ketorolac: (±)-5-benzoyl-2,3-dihydro-1H-pyrrolizine-1-carboxylic acid, 2-amino-2-(hydroxymethyl)-1,3-propanediol.

The chemical structure of ketorolac is represented by:

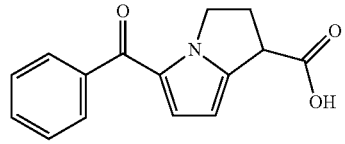 [SMILES: O=C(c1ccccc1)c1ccc2n1CCC2C(=O)O]

(IV) Oils

Oils which may be used in the compositions of the present invention, in particular emulsions, and which may be used in combinations of oils including two or more oils and in combination with surfactants, in combinations of two or more surfactants, include but are not limited to:

Anise oil; Castor oil; Clove oil; Cassia oil; Cinnamon oil; oils having a specific gravity between 0.90 and 0.95; Almond oil; Corn oil; Arachis oil; Cottonseed oil; Safflower oil; Maize oil; Linseed oil; Rapeseed oil; Soybean oil; Olive oil; Caraway oil; Rosemary oil; Peanut oil; Peppermint oil; Sunflower oil; Eucalyptus oil; Sesame oil; an oil having a specific gravity below 0.9; Mineral oil; Coriander oil; Lavender oil; Citronella oil; Juniper oil; Lemon oil; Orange oil; Clary sage oil; Nutmeg oil; and Tea tree oil.

(V) Surfactants

Surfactants which may be used in the present invention in combination with one or more oils and in combination with one or more surfactants, include, but are not limited to:

Alcohols, including but not limited to:

Diglycerol®, which is available from Solvay Chemicals, Inc.; Hetoxide GT-80®, which is available from Global-Seven, Inc.; Lexemul BEO®, which is available from Inolex Chemical Co.; Polyglycerol-3®, which is available from Solvay Chemicals, Inc.; Redicote E Series®, which is available from Akzo Nobel Surface Chemistry LLC; Simulsol OX 1005L®, which is available from Seppic Inc.; Stanfax 567®, which is available from Para-Chem Standard Div.; TA-1618®, which is available from Procter & Gamble; and Witconol H-31A®, which is available from Akzo Nobel Surface Chemistry LLC.

Amine Oxides, including but not limited to:

AO-405®, which is available from Tomah Products®, Inc.; AO-455®, which is available from Tomah Products®, Inc.; AO 728 Special®, which is available from Tomah Products®, Inc.; Barlox 12®, which is available from Lonza Inc.; Barlox 14®, which is available from Lonza Inc.; Burcoxide Lo®, which is available from Burlington Chemical Co.®, Inc.; Caloxamine LO®, which is available from Pilot Chemical Co.; Chemoxide CAW®, which is available from Chemron Corp.; Chemoxide LM-30®, which is available from Chemron Corp.; Chemoxide LO®, which is available from Chemron Corp.; Chemoxide MO®, which is available from Chemron Corp.; Colalux CAO-35®, which is available from Colonial Chemical Co.; Colalux LO®, which is available from Colonial Chemical Co.; DeMox CAPO®, which is available from DeForest Enterprises, Inc.; DeMox CSG-30®, which is available from DeForest Enterprises, Inc.; DeMox LAO®, which is available from DeForest Enterprises, Inc.; Emcol L®, which is available from Crompton Corp.; Empigen OB®, which is available from Huntsman LLC; Empigen OS/A®, which is available from Huntsman LLC; Foamox CDO®, which is available from Alzo International, Inc.; Foamox DMM®, which is available from Alzo International, Inc.; Foamox DMS®, which is available from Alzo International, Inc.; Genaminox KC®, which is available from Clariant Corporation; Genaminox LA®, which is available from Clariant Corporation; Hartofoam SAO®, which is available from Hart Chemical Corp.; Hartox DMCD®, which is available from Hart Chemical Corp.; Lipowax DAT®, which is available from Lipo Chemicals, Inc.; Lipowax PB Pastilles®, which is available from Lipo Chemicals, Inc.; Mackamine C8®, which is available from The McIntyre Group; Mackamine C10®, which is available from The McIntyre Group; Mackamine C14®, which is available from The McIntyre Group; Mackamine CAO®, which is available from The McIntyre Group; Mackamine CO®, which is available from The McIntyre Group; Mackamine LO®, which is available from The McIntyre Group; Mackamine O$_2$®, which is available from The McIntyre Group; Mackamine SAO®, which is available from The McIntyre Group; Mackamine SO®, which is available from The McIntyre Group; Mazox KCAO®, which is available from BASF Corp.; Monalac MO®, which is available from Uniqema; Norfox LDA®, which is available from Norman, Fox & Co.; Rhodamox LO®, which is available from Rhodia, Inc.; Schercamox C-AA®, which is available from Noveon®, Inc.; Schercamox DMA®, which is available from Noveon®, Inc.; Schercamox DML®, which is available from Noveon®, Inc.; Schercamox DMM®, which is available from Noveon®, Inc.; Schercamox DMS®, which is available from Noveon®, Inc.; Tegotens DO®, which is available from Goldschmidt Chemical Corp.; Tomah AO-14-2®, which is available from Tomah Products®, Inc.; Triaminox CDO®, which is available from Tri-Tex Co.®, Inc.; Mazox CDA CG®; and Standamox CAW®.

Block Polymers, including, but not limited to:

AL 2070®, which is available from Uniqema; Antarox 17-R-2®, which is available from Rhodia, Inc.; Antarox 25-R-2®, which is available from Rhodia, Inc.; Antarox 31-R-1®, which is available from Rhodia, Inc.; Antarox P-84®, which is available from Rhodia, Inc.; Antarox P-104/H®, which is available from Rhodia, Inc.; Arnox BP-Series®, which is available from Crompton Corp.; Chemonic 435®, which is available from Chemron Corp.; Chemonic D-25®, which is available from Chemron Corp.; Chemonic PL Series®, which is available from Chemron Corp.; Ethox L-121®, which is available from Ethox Chemicals, LLC; Ethox L-122®, which is available from Ethox Chemicals, LLC; Genapol PF-10®, which is available from Clariant Corporation; Genapol PF-20®, which is available from Clariant Corporation; Genapol PF-40A®, which is available from Clariant Corporation; Norfox 2-LF®, which is available from Norman, Fox & Co.; Pluronic, which is available from BASF; Simulsol NW 342®, which is available from Seppic Inc.; T-Det BP-1®, which is available from Harcros Chemicals Inc.; T-Det XD®, which is available from Harcros Chemicals Inc.; T-Det XH®, which is available from Harcros Chemicals Inc.; Triton CF-32®, which is available from Dow Chemical Company; Witconol 171®, which is available from Akzo Nobel Surface Chemistry LLC; Witconol 324®, which is available from Akzo Nobel Surface Chemistry LLC; Witconol 324D®, which is available from Akzo Nobel Surface Chemistry LLC; Witconol PD-2000®, which is available from Akzo Nobel Surface Chemistry LLC; Chemal BP 261®; Chemal BP 262®; Chemal BP 3172®; Chemal BP 3174®; Pluronic 10R5®; Pluronic 1782®; Pluronic 17R4®; Pluronic 2582®; Pluronic 25R4®; Pluronic 31R1®; Pluronic F108®; Pluronic F127®; Pluronic F38®; Pluronic F68®; Pluronic F68LF®; Pluronic F77®; Pluronic F87®; Pluronic F88®; Pluronic F98®; Pluronic L10®; Pluronic L101®; Pluronic L121®; Pluronic L31®; Pluronic L35®; Pluronic L43®; Pluronic L44®; Pluronic L61®; Pluronic L62®; Pluronic L62D®; Pluronic L62LF®; Pluronic L64®; Pluronic L81®; Pluronic L92®; Pluronic P103®; Pluronic P104®; Pluronic P105®; Pluronic P123®; Pluronic P65®; Pluronic P84®; Pluronic P85®; Surfonic POA-17R2®; Surfonic POA-2582®; Tetronic 1107®; Tetronic 1307®; Tetronic 150R1®; Tetronic 304®; Tetronic 701®; Tetronic 901®; Tetronic 904®; Tetronic 908®; and Tetronic 90R4®.

Carboxylated Alcohols or Alkylphenol Ethoxylates, including but not limited to,

Emcol CN-6®, which is available from Crompton Corp.; Ethcarb®, which is available from Ethox Chemicals, LLC; Gemtex WNT-Conc®, which is available from Finetex Inc.; Incrodet TD7-C®, which is available from Croda Inc.; Marlinat CM 105/80®, which is available from Sasol North America Inc.; Marlowet 1072®, which is available from Sasol North America Inc.; Marlowet 4530®, which is available from Sasol North America Inc.; Marlowet 4530 LF®, which is available from Sasol North America Inc.; Marlowet 4534®, which is available from Sasol North America Inc.; Marlowet 4538®, which is available from Sasol North America Inc.; Marlowet 4539®, which is available from Sasol North America Inc.; Marlowet 4539 LF®, which is available from Sasol North America Inc.; Marlowet 4541®, which is available from Sasol North America Inc.; Miranate LEC-80®, which is available from Rhodia, Inc.; Sandopan B®, which is available from Clariant Corporation; Sandopan B Modified®, which is available from Clariant Corporation; Sandopan LS-24 Gel®, which is available from Clariant Corporation; Surfine T-A®, which is available from Finetex Inc.; and Surfine AZI-A.

Carboxylic Acids/Fatty Acids, including, but not limited to:

Colaterge RAM®, which is available from Colonial Chemical Co.; Colatrope INC®, which is available from Colonial Chemical Co.; Crodacid B®, which is available from Croda Inc.; DeTrope CA-100®, which is available from DeForest Enterprises, Inc.; Latol MTO®, which is available from Georgia-Pacific Corp.; Lumulse CC-33 K®, which is available from Lambent Technologies Corp.; Mulls 2218®, which is available from Bernel Chemical Co.®, Inc.; OL-600®, which is available from Procter & Gamble; OL-800®, which is available from Procter & Gamble; R-910®, which is available from Procter & Gamble; S-210®, which is available from Procter & Gamble; Sandopan DTC Acid®, which is available from Clariant Corporation; Sandopan LS 24 N®, which is available from Clariant Corporation; and Sandopan MA-18®, which is available from Clariant Corporation.

Ethoxylated Alcohols, including, but not limited to,

Adsee 799®, which is available from Akzo Nobel Surface Chemistry LLC; Adsee 799®, which is available from Crompton Corp.; Alfonic 610-3.5®, which is available from Sasol North America Inc.; Alfonic 810-2®, which is available from Sasol North America Inc.; Alfonic 810-6®, which is available from Sasol North America Inc.; Alfonic 1012-3®, which is available from Sasol North America Inc.; Alfonic 1012-5®, which is available from Sasol North America Inc.; Alfonic 1216CO-1.5®, which is available from Sasol North America Inc.; Alfonic 1216CO-7®, which is available from Sasol North America Inc.; Alfonic 1412-3®, which is available from Sasol North America Inc.; Alfonic 1412-7®, which is available from Sasol North America Inc.; Arlasolve 200®, which is available from Uniqema; Arlasolve 200 Liquid®, which is available from Uniqema; Armix 180-C®, which is available from Crompton Corp.; Armix 183®, which is available from Crompton Corp.; Armul 2404®, which is available from Akzo Nobel Surface Chemistry LLC; Armul 2404®, which is available from Crompton Corp.; Atlas EMJ-C®, which is available from Atlas Refinery Inc.; Atlas G-2109®, which is available from Uniqema; Atlas G-3886®, which is available from Uniqema; Atlas G-3890®, which is available from Uniqema; Bio Soft E-200®, which is available from Stepan Canada Inc.; Bio Soft E-300®, which is available from Stepan Canada Inc.; Bio Soft E-400®, which is available from Stepan Canada Inc.; Bio Soft EN 600®, which is available from Stepan Canada Inc.; Bio Soft TD-400®, which is available from Stepan Canada Inc.; Bio Soft TD-630®, which is available from Stepan Canada Inc.; Brij 30®, which is available from Uniqema; Brij 52®, which is available from Uniqema; Brij 56®, which is available from Uniqema; Brij 58®, which is available from Uniqema; Brij 72®, which is available from Uniqema; Brij 76®, which is available from Uniqema; Brij 78®, which is available from Uniqema; Brij 93®, which is available from Uniqema; Brij 97®, which is available from Uniqema; Brij 98®, which is available from Uniqema; Brij 700®, which is available from Uniqema; Brij 700 S®, which is available from Uniqema; Brij 721®, which is available from Uniqema; Brij 721 S®, which is available from Uniqema; Burcoterge CDG®, which is available from Burlington Chemical Co.®, Inc.; Canasol AT 600®, which is available from Canamex Quimicos S.A de C.v; Canasol AT 800®, which is available from Canamex Quimicos S.A de C.v; Canasol AT 1200®, which is available from Canamex Quimicos S.A de C.v; Canasol BJ 35®, which is available from Canamex Quimicos S.A de C.v; Canasol BJ 36®, which is available from Canamex Quimicos S.A de C.v; Canasol BJ 52®, which is available from Canamex Quimicos S.A de C.v; Canasol BJ 58®, which is available from Canamex Quimicos S.A de C.v; Canasol BJ 72®, which is available from Canamex Quimicos S.A de C.v; Canasol BJ 78®, which is available from Canamex Quimicos S.A de C.v; Canasol BJ 98®, which is available from Canamex Quimicos S.A de C.v; Canasol BJ 307®, which is available from Canamex Quimicos S.A de C.v; Cerfak 1400®, which is available from Houghton International Inc.; Cetomacrogol 1000 BP®, which is available from Croda Inc.; Chemonic C-2®, which is available from Chemron Corp.; Chemonic C-10®, which is available from Chemron Corp.; Chemonic C-20®, which is available from Chemron Corp.; Chemonic CT-12®, which is available from Chemron Corp.; Chemonic CT-20®, which is available from Chemron Corp.; Chemonic CT-30®, which is available from Chemron Corp.; Chemonic CT-55®, which is available from Chemron Corp.; Chemonic G-7®, which is available from Chemron Corp.; Chemonic G-26®, which is available from Chemron Corp.; Chemonic L-4®, which is available from Chemron Corp.; Chemonic L-7®, which is available from Chemron Corp.; Chemonic L-12®, which is available from Chemron Corp.; Chemonic L-23®, which is available from Chemron Corp.; Chemonic O-2®, which is available from Chemron Corp.; Chemonic O-5®, which is available from Chemron Corp.; Chemonic O-10®, which is available from Chemron Corp.; Chemonic O-20®, which is available from Chemron Corp.; Chemonic S-2®, which is available from Chemron Corp.; Chemonic S-10®, which is available from Chemron Corp.; Chemonic S-20®, which is available from Chemron Corp.; Colamulse FE®, which is available from Colonial Chemical Co.; Cremophor A 20®, which is available from BASF Corp.; Cremophor SA 2®, which is available from BASF Corp.; Dehydrol 100®, which is available from Cognis Canada Corp.; Dehydrol O-4®, which is available from Cognis Canada Corp.; DeIonic C-18®, which is available from DeForest Enterprises, Inc.; DeSonic 6T®, which is available from Crompton Corp.; DeSonic 9D®, which is available from Crompton Corp.; DeSonic 9T®, which is available from Crompton Corp.; DeSonic 12D®, which is available from Crompton Corp.; DeSonic 12T®, which is available from Crompton Corp.; DeSonic 15T®, which is available from Crompton Corp.; DeSonic TDA-9®, which is available from Crompton Corp.; DeThox GLG-7®, which is available from DeForest Enterprises, Inc.; DeThox GLG-26®, which is available from DeForest Enterprises, Inc.; DeThox LA-4®, which is available from DeForest Enterprises, Inc.; DeThox LA-23®, which is available from DeForest Enterprises, Inc.; DeThox SA-80®, which is available from DeForest Enterprises, Inc.; Disponil O5®, which is available from Cognis Corporation; Eccoterge EO-41B®, which is available from Eastern Color & Chemical Co.; Empilan KA2.5/90®, which is available from Huntsman LLC; Empilan KA5/90®, which is available from Huntsman LLC; Empilan KM-20®, which is available from Huntsman LLC; Empilan KM-50®, which is available from Huntsman LLC; Empilan L-23®, which is available from Huntsman LLC; Ethylan 25-3®, which is available from Akzo Nobel Surface Chemistry LLC; Ethylan 1204®, which is available from Akzo Nobel Surface Chemistry LLC; Ethylan DA-4®, which is available from Akzo Nobel Surface Chemistry LLC; Ethylan LA-230®, which is available from Akzo Nobel Surface Chemistry LLC; Ethylan SN®, which is available from Akzo Nobel Surface Chemistry LLC; Ethylan TD-60®, which is available from Akzo Nobel Surface Chemistry LLC; Ethylan TD-100®, which is available from Akzo Nobel Surface Chemistry LLC; Ethylan TD-1407®, which is available from Akzo Nobel Surface Chemistry LLC; Eumulgin B1®, which is available from Cognis Canada Corp.; Eumulgin B2®, which is available from Cognis Canada Corp.; Eumulgin B3®, which is available from Cognis Canada Corp.; Eumulgin 0-10®, which is available from Cognis Canada Corp.; Flo Mo 80/20®, which is available from Crompton Corp.; Flo Mo Low Foam®, which is available from Crompton Corp.; Forlan C-24®, which is available from RITA Corp.; Genapol 1454®, which is available from Clariant Corporation; Genapol BA-020®, which is available from Clariant Corporation; Genapol BA-040®, which is available from Clariant Corporation; Genapol C-100®, which is available from Clariant Corporation; Genapol DA 060®, which is available from Clariant Corporation; Genapol HS 020®, which is available from Clariant Corporation; Genapol HS 200®, which is available from Clariant Corporation; Genapol ID-040®, which is available from Clariant Corporation; Genapol ID-060®, which is available from Clariant Corporation; Genapol ID-090®, which is available from Clariant Corporation; Genapol LA 010®, which is available from Clariant Corporation; Genapol LA 020®, which is available from Clariant Corporation; Genapol LA 030®, which is available from Clariant Corporation; Genapol LA 040®, which is available from Clariant Corporation; Genapol LA 050®, which is available from Clariant Corporation; Genapol LA 060®, which is available from Clariant Corporation; Genapol LA 070®, which is available from Clariant Corporation; Genapol LA 070S®, which is available from Clariant Corporation; Genapol LA 230®, which is available from Clariant Corporation; Genapol O 020®, which is available from Clariant Corporation; Genapol O 050®, which is available from Clariant Corporation; Genapol O 100®, which is available from Clariant Corporation; Genapol O 200®, which is available from Clariant Corporation; Genapol SA 030®, which is available from Clariant Corporation; Genapol SA 120®, which is available from Clariant Corporation; Genapol T-020®, which is available from Clariant Corporation; Genapol UD-030®, which is available from Clariant Corporation; Genapol UD-050®, which is available from Clariant Corporation; Genapol UD-070®, which is available from Clariant Corporation; Genapol UD-079®, which is available from Clariant Corporation; Genapol UD-080®, which is available from Clariant Corporation; Genapol UD-110®, which is available from Clariant Corporation; Genapol X 030®, which is available from Clariant Corporation; Genapol X 050®, which is available from Clariant Corporation; Genapol X 060®, which is available from Clariant Corporation; Genapol X 070®, which is available from Clariant Corporation; Genapol X 080®, which is available from Clariant Corporation; Genapol X 100®, which is available from Clariant Corporation; Genapol X159®, which is available from Clariant Corporation; Generol 122 E5®, which is available from Cognis Canada Corp.; Generol 122 E25®, which is available from Cognis Canada Corp.; Hostacerin T-3®, which is available from Clariant Corporation; Iconol LF 110®, which is available from BASF Corp.; Incropol CS-20®, which is available from Croda Inc.; Lexemul CS-20®, which is available from Inolex Chemical Co.; Liponic EG-1®, which is available from Lipo Chemicals, Inc.; Lipowax D®, which is available from Lipo Chemicals, Inc.; Lipowax G®, which is available from Lipo Chemicals, Inc.; Lipowax NI®, which is available from Lipo Chemicals, Inc.; Lipowax P®, which is available from Lipo Chemicals, Inc.; Lipowax P-31®, which is available from Lipo Chemicals, Inc.; Lipowax PR®, which is available from Lipo Chemicals, Inc.; Lumulse CS-20®, which is available from Lambent Technologies Corp.; Macol CSA-20®, which is available from BASF Corp.; Marlox B 24/50®, which is available from Sasol North America Inc.; Mazawet 77®, which is available from BASF Corp.; Norfox 1713®, which is available from Norman, Fox & Co.; Norfox 2579®, which is available from Norman, Fox & Co.; Norfox Lo Foam®, which is available from Norman, Fox & Co.; Promulgen D®, which is available from Amerchol Corp.; Promulgen G®, which is available from Amerchol Corp.; Renex 30®, which is available from Uniqema; Renex 36®, which is available from Uniqema; Rhodasurf A 24®, which is available from Rhodia, Inc.; Rhodasurf AAE-10®, which is available from Rhodia, Inc.; Rhodasurf BEH-25®, which is available from Rhodia, Inc.; Rhodasurf BEH-40®, which is available from Rhodia, Inc.; Rhodasurf DA 530®, which is available from Rhodia, Inc.; Rhodasurf DA 630®, which is available from Rhodia, Inc.; Rhodasurf DA 639®, which is available from Rhodia, Inc.; Rhodasurf LAN-23®, which is available from Rhodia, Inc.; Rhodasurf ON-870®, which is available from Rhodia, Inc.; Rhodasurf ON-877®, which is available from Rhodia, Inc.; Rhodasurf TB-970 FLK®, which is available from Rhodia, Inc.; Ritacet-20®, which is available from RITA Corp.; Ritachol 1000®, which is available from RITA Corp.; Ritachol 2000®, which is available from RITA Corp.; Ritachol 5000®, which is available from RITA Corp.; Ritox 35®, which is available from RITA Corp.; Surfonic DA-4®, which is available from Huntsman LLC; Surfonic DA-6®, which is available from Huntsman LLC; Surfonic L46-7®, which is available from Huntsman LLC; Surfonic POA®, which is available from Huntsman LLC; Synthrapol KB®, which is available from Uniqema; Teginacid®, which is available from Goldschmidt Chemical Corp.; Teginacid C®, which is available from Goldschmidt Chemical Corp.; Tegotens EC 11®, which is available from Goldschmidt Chemical Corp.; Tinegal NA®, which is available from Ciba Specialty Chemicals Corp.; Tomadol 400®, which is available from Tomah Products®, Inc.; Tomadol 600®, which is available from Tomah Products®, Inc.; Tomadol 900®, which is available from Tomah Products®, Inc.; Uniperol O®, which is available from BASF Corp.; Witconol SN Series®, which is available from Crompton Corp.; T-Det EPO-64®; T-Det N-1.5®; T-Det N-10.5®; T-Det N-100®; T-Det N-1007®; T-Det N-12®; T-Det N-14®; T-Det N-20®; T-Det N-30®; T-Det N-307®; T-Det N-4®; T-Det N-40®; T-Det N-407®; T-Det N-50®; T-Det N-507®; T-Det N-6®; T-Det N-70®; T-Det N-8®; T-Det N-9.5®; T-Det O-12®; Abex 2515®; Abex 2525/40®; Abex 2535®; Abex 2545®; Alfonic 1216CO-9®; Alfonic 1412-3®; Alfonic TDA-12®; Alfonic TDA-3®; Alfonic TDA-4®; Alfonic TDA-6®; Alfonic TDA-7®; Alfonic TDA-8®; Alfonic TDA-9®; Ameroxol OE-10®; Ameroxol OE-2®; Ameroxol OE-20®; Armix 176®; Armix 180-C®; Armix 183®; Brij 35®; Brij 35 Liquid®; Brij 35 SP®; Canasol MJ 2109®; Canasol MJ 52®; Canasol R 3600®; Canasol R 3603®; Canasol R 40001-1®; Chemal DA-4®; Chemal DA-6®; Chemal DA-9®; Chemal LA-23®; Chemal LA-4®; Chemal LA-9®; Chemal OA-20G®; Chemal OA-5®; Chemal OA-9®; Chemal TDA-12®; Chemal TDA-15®; Chemal TDA-3®; Chemal TDA-6®; Chemal TDA-9®; DeSonic TDA-9®; Ethal EH-2®; Ethal EH-5®; Ethal OA-23®; Ethosperse CA-20®; Ethosperse LA-12®; Ethosperse LA-23®; Ethosperse LA-4®; Ethylan SN-120®; Ethylan SN-70®; Ethylan SN-90®; Generol 122 E25®; Hetoxol C-24®; Hetoxol CA-10®; Hetoxol CA-2®; Hetoxol CA-20®; Hetoxol CAWS®; Hetoxol CD-3®; Hetoxol CD-4®; Hetoxol CS-15®; Hetoxol CS-20®; Hetoxol CS-20D®; Hetoxol CS-25®; Hetoxol CS-50®; Hetoxol CS-9®; Hetoxol CSA-15®; Hetoxol D®; Hetoxol G®; Hetoxol J®; Hetoxol L®; Hetoxol L-23®; Hetoxol L-4®; Hetoxol L-9®; Hetoxol LS-9®; Hetoxol M-3®; Hetoxol OA-10 Special®; Hetoxol OA-20 Special®; Hetoxol OA-3 Special®; Hetoxol OA-5 Special®; Hetoxol OL-10®; Hetoxol OL-2®; Hetoxol OL-23®; Hetoxol OL-4®; Hetoxol OL-40®; Hetoxol OL-5®; Hetoxol PLA®; Hetoxol SP-15®; Hetoxol STA-10®; Hetoxol STA-2®; Hetoxol STA-30®; Hetoxol TD-12®; Hetoxol TD-18®; Hetoxol TD-3®; Hetoxol TD-6®; Hetoxol TD-9®; Hetoxol TDEP-15®; Hetoxol TDEP-63®; Iconol 24-12®; Iconol 24-23®; Iconol 24-4®; Iconol DA-4®; Iconol DA-6®; Iconol TDA-10®; Iconol TDA-3®; Iconol TDA-6®; Iconol TDA-8-90%®; Iconol TDA-9®; Lexemul CS-20®; Lipocol C-10®; Lipocol C-2®; Lipocol C-20®; Lipocol L-12®; Lipocol L-23®; Lipocol L-4®; Lipocol O-10®; Lipocol O-2®; Lipocol O-20®; Lipocol O-5®; Lipocol S-10®; Lipocol S-2®; Lipocol S-20®; Lipocol SC-15®; Lipocol SC-20®; Lipocol SC-4®; Lipocol TD-12®; Marlox B 24/80®; Myrj 45®; Myrj 52®; Myrj 52S®; Myrj 53®; Myrj 59®; Plurafac A-38®; Plurafac B-25-5®; Plurafac B-26®; Plurafac D-25®; Plurafac LF 131®; Plurafac LF 4030®; Plurafac LF 7000®; Plurafac RA-20®; Plurafac RA-30®; Plurafac RA-40®; Rhodasurf BC-420®; Rhodasurf BC-610®; Rhodasurf BC-630®; Rhodasurf BC-720®; Rhodasurf BC-840®; Rhodasurf L 1®; Rhodasurf L 12®; Rhodasurf L 2®; Rhodasurf L 20®; Rhodasurf L 3®; Rhodasurf L 30®; Rhodasurf L 4®; Rhodasurf L 50®; Rhodasurf L 7/90®; Rhodasurf LA-3®; Rhodasurf LA-7®; Rhodasurf LAN-23®; Rhodasurf ON-870®; Rhodasurf ON-877®; Rhodasurf TDA-8/5®; Ritapro 100®; Ritapro 165®; Ritapro 200®; Ritapro 300®; Ritoleth 10®; Ritoleth 2®; Ritoleth 20®; Ritoleth 5®; Solulan 16®; Solulan 75®; Solulan C-24®; Solulan L-575®; Surfonic TDA-11®; Surfonic TDA-3B®; Surfonic TDA-6®; Surfonic TDA-6/88®; Surfonic TDA-8®; Surfonic TDA-8/90®; Surfonic TDA-9®; T-Det A106®; T-Det A109®; T-Det A136®; T-Det A139®; T-Det A2412®; T-Det A243®; T-Det A247®; T-Det A249®; T-Det A467®; T-Det COE®; T-Det DD-10®; T-Det DD-A®; T-Det DD-7®; T-Det EPO-104®; T-Det EPO-61®; T-Det EPO-62®; T-Det O-165®; T-Det O-307®; T-Det O-40®; T-Det O-407®; T-Det O-6®; T-Det O-8®; T-Det O-9®; Tergitol 15-S-12®; Tergitol 15-S-15®; Tergitol 15-S-20®; Tergitol 15-S-20 (80AQ)®; Tergitol 15-S-3®; Tergitol 15-S-30®; Tergitol 15-S-40®; Tergitol 15-S-40 (70AQ)®; Tergitol 15-S-5®; Tergitol 15-S-7®; Tergitol 15-S-9®; Tergitol L-101®; Tergitol L-61®; Tergitol L-62®; Tergitol L-64®; Tergitol L-81®; Tergitol NP-10®; Tergitol NP-11®; Tergitol NP-12®; Tergitol NP-13®; Tergitol NP-15®; Tergitol NP-30®; Tergitol NP-30 (70 AQ)®; Tergitol NP-4®;Tergitol NP-40®; Tergitol NP-40 (70 AQ)®; Tergitol NP-50 (70 AQ)®; Tergitol NP-55 (70 AQ)®; Tergitol NP-6®; Tergitol NP-7®; Tergitol NP-70 (70 AQ)®; Tergitol NP-8®; Tergitol NP-9®; Tergitol NP-9.5®; Tergitol TMN-10®; Tergitol TMN-3®; Tergitol TMN-6®; Tergitol XD®; Tergitol XH®; Tergitol XJ®; Tornadol 1-3®; Tornadol 1-5®; Tornadol 1-7®; Tornadol 23-1®; Tornadol 23-3®; Tornadol 23-5®; Tornadol 23-6.5®; Tornadol 25-12®; Tornadol 25-3®; Tornadol 25-7®; Tornadol 25-9®; Tornadol 45-13®; Tornadol 45-2.5®; Tornadol 45-7®; Tornadol 91-2.5®; Tornadol 91-6®; Tornadol 91-8®; Volpo S-10®; Volpo S-2®; Volpo S-20®; Volpo-10®; Volpo-20®; Volpo-3®; and Volpo-5®.

Ethoxylated Alkylphenols, including, but not limited to:

Antarox LF-222®, which is available from Rhodia, Inc.; Atlox 775®, which is available from Uniqema; Caloxylate N-9®, which is available from Pilot Chemical Co.; Canasol NF-1000®, which is available from Canamex Quimicos S.A de C.v; Canasol NF-3000®, which is available from Canamex Quimicos S.A de C.v; Canasol NF-3070®, which is available from Canamex Quimicos S.A de C.v; Canasol OF 1670®, which is available from Canamex Quimicos S.A de C.v; Canasol OF 2570®, which is available from Canamex Quimicos S.A de C.v; Canasol OF 4070®, which is available from Canamex Quimicos S.A de C.v; Chemax DNP-8®, which is available from Chemax Performance Solutions; Chemax DNP-18®, which is available from Chemax Performance Solutions; Chemax DNP-150/50®, which is available from Chemax Performance Solutions; DeSonic 1.5N®, which is available from Crompton Corp.; DeSonic 4N®, which is available from Crompton Corp.; DeSonic 5N®, which is available from Crompton Corp.; DeSonic 6D®, which is available from Crompton Corp.; DeSonic 6N®, which is available from Crompton Corp.; DeSonic 7N®, which is available from Crompton Corp.; DeSonic 9N®, which is available from Crompton Corp.; DeSonic 10D®, which is available from Crompton Corp.; DeSonic 11N®, which is available from Crompton Corp.; DeSonic 12N®, which is available from Crompton Corp.; DeSonic 15N®, which is available from Crompton Corp.; DeSonic 20N®, which is available from Crompton Corp.; Eccoscour RC®, which is available from Eastern Color & Chemical Co.; Eccoterge EO-100®, which is available from Eastern Color & Chemical Co.; Emulsifier 632/90%®, which is available from Ethox Chemicals, LLC; Geronol AG-821®, which is available from Rhodia, Inc.; Gradonic N-95®, which is available from Graden Chemical Co. Inc.; Hetoxide NP-4®, which is available from Global-Seven, Inc.; Hetoxide NP-30®, which is available from Global-Seven, Inc.; Hostapal N-100®, which is available from Clariant Corporation; Hostapal N-110®, which is available from Clariant Corporation; Igepal CTA-639W®, which is available from Rhodia, Inc.; Igepal DAP-9®, which is available from Rhodia, Inc.; Igepal OD-410®, which is available from Rhodia, Inc.; Igepal SS-837®, which is available from Rhodia, Inc.; Lipocol NP-9 USP®, which is available from Lipo Chemicals, Inc.; Macol DNP-10®, which is available from BASF Corp.; Marlophen NP 5®, which is available from Sasol North America Inc.; Marlophen P 1®, which is available from Sasol North America Inc.; Surfonic NB®, which is available from Huntsman LLC; Surfonic OPB-307®, which is available from Huntsman LLC; Surfonic OPB-407®, which is available from Huntsman LLC; Syn Fac 334®, which is available from Milliken Chemical; Syn Fac 8216®, which is available from Milliken Chemical; Triton N-57®, which is available from Dow Chemical Company; Trycol 6956®, which is available from Cognis Corporation; Trycol 6961®, which is available from Cognis Corporation; Trycol 6964®, which is available from Cognis Corporation; Trycol 6969®, which is available from Cognis Corporation; Trycol 6974®, which is available from Cognis Corporation; Witbreak DRB-127®, which is available from Akzo Nobel Surface Chemistry LLC; Witbreak DRB-127®, which is available from Crompton Corp.; and Witconol NP Series®, which is available from Akzo Nobel Surface Chemistry LLC; Delonic NPE-100®; Delonic NPE-30®; Delonic NPE-40®; Delonic OPE-10®; Delonic OPE-12®; Delonic OPE-30®; Delonic OPE-40®; Delonic OPE-5®; Delonic OPE-7.5®; DeSonic S-100®; DeSonic S-114®; DeSonic S-405®; DeSonic S-45®; Igepal CA-210®; Igepal CA-407®; Igepal CA-420®; Igepal CA-520®; Igepal CA-620®; Igepal CA-630®; Igepal CA-720®; Igepal CA-877®; Igepal CA-887®; Igepal CA-897®; Igepal CO-210®; Igepal CO-430®; Igepal CO-520®; Igepal CO-530®; Igepal CO-610®; Igepal CO-630®; Igepal CO-630 Special®; Igepal CO-660®; Igepal CO-710®; Igepal CO-720®; Igepal CO-730®; Igepal CO-738®; Igepal CO-850®; Igepal CO-880®; Igepal CO-887®; Igepal CO-890®; Igepal CO-897®; Igepal CO-970®; Igepal CO-977®; Igepal CO-987®; Igepal CO-990 FLK®; Igepal CO-997®; Igepal DM-430®; Igepal DM-530®; Igepal DM-710®; Igepal DM-730®; Igepal DM-880®; Igepal DM-970 FLK®; Igepal OD-410®; Igepal RC-520®; Igepal RC-620®; Igepal RC-630®; Norfox NP-12®; Norfox NP-4®; Norfox NP-6®; Norfox NP-887®; Norfox NP-9®; Norfox NP-977®; Norfox OP-100®; Norfox OP-102®; Norfox OP-114®; Norfox OP-45®; Surfonic N-10®; Surfonic N-100®; Surfonic N-102®; Surfonic N-120®; Surfonic N-150®; Surfonic N-200®; Surfonic N-300®; Surfonic N-31.5®; Surfonic N-40®; Surfonic N-400®; Surfonic N-60®; Surfonic N-85®; Surfonic N-95®; Surfonic NB-18®; Surfonic NB-23®; Surfonic NB-25®; Surfonic NB-307®; Surfonic NB-31®; Surfonic NB-41®; Surfonic NB-43®; Surfonic OP-100®; Surfonic OP-120®; Surfonic OP-15®; Surfonic OP-35®; Surfonic OP-70®; Triton X-100®; Triton X-102®; Triton X-114®; Triton X-15®; Triton X-165 (70%)®; Triton X-207®; Triton X-305 (70%)®; Triton X-35®; Triton X-405 (70%)®; Triton X-45®; and Triton X-705 (70%)®.

Ethoxylated Aryl Phenols, including but not limited to,

Soprophor BSU®, which is available from Rhodia, Inc.; Soprophor CY/8®, which is available from Rhodia, Inc.; Soprophor S/25®, which is available from Rhodia, Inc.; Witconol NIO®, which is available from Akzo Nobel Surface Chemistry LLC; Witconol NIW®, which is available from Akzo Nobel Surface Chemistry LLC; Witconol S-100®, which is available from Akzo Nobel Surface Chemistry LLC; Cedepal CA-210®; Cedepal CA-520®; Cedepal CA-630®; Cedepal CA-720®; Cedepal CA-890®; Cedepal CA-897®; Cedepal CO-210®; Cedepal CO-430®; Cedepal CO-530®; Cedepal CO-630®; Cedepal CO-710®; Cedepal CO-730®; Cedepal CO-880®; Cedepal CO-887®; Cedepal CO-890®; Cedepal CO-897®; Cedepal CO-970®; Cedepal CO-977®; Cedepal CO-990®; and Cedepal CO-997®.

Ethoxylated Fatty Acids, including, but not limited to:

Aldo PGHMS®, which is available from Lonza Inc.; Alkamuls TO-15/HR®, which is available from Rhodia, Inc.; Armotan AL-69-66®, which is available from Akzo Nobel Surface Chemistry LLC; Cerasynt 840®, which is available from International Specialty Product/IS; Cerasynt 945®, which is available from International Specialty Products/IS; Crystal Inhibitor No. 5®, which is available from Harcros Chemicals Inc.; DeThox Acid L-9®, which is available from DeForest Enterprises, Inc.; DeThox Acid S-8®, which is available from DeForest Enterprises, Inc.; Ethofat 242/25®, which is available from Akzo Nobel Surface Chemistry LLC; Hydropalat 65®, which is available from Cognis Corporation; Lipo EGMS®, which is available from Lipo Chemicals, Inc.; Lipopeg 2 DL®, which is available from Lipo Chemicals, Inc.; Lipopeg 4 DL®, which is available from Lipo Chemicals, Inc.; Lipopeg 4-L®, which is available from Lipo Chemicals, Inc.; Lipopeg 39-5®, which is available from Lipo Chemicals, Inc.; Lipopeg 4-5®, which is available from Lipo Chemicals, Inc.; Lipopeg 10-S®, which is available from Lipo Chemicals, Inc.; Lipopeg 100-S®, which is available from Lipo Chemicals, Inc.; Lipopeg 6000 DS®, which is available from Lipo Chemicals, Inc.; Lumulse 40-L®, which is available from Lambent Technologies Corp.; Lumulse 40-S®, which is available from Lambent Technologies Corp.; Lumulse 42-L®, which is available from Lambent Technologies Corp.; Lumulse 42-S®, which is available from Lambent Technologies Corp.; Lumulse 100-S®, which is available from Lambent Technologies Corp.; Lumulse 602-S®, which is available from Lambent Technologies Corp.; Magrabar PGE-20-0®, which is available from Magrabar Chemical Corp.; Magrabar PGE-20L®, which is available from Magrabar Chemical Corp.; Magrabar PGE-20T®, which is available from Magrabar Chemical Corp.; Magrabar PGE-22-0®, which is available from Magrabar Chemical Corp.; Magrabar PGE-22L®, which is available from Magrabar Chemical Corp.; Magrabar PGE-22T®, which is available from Magrabar Chemical Corp.; Magrabar PGE-40-0®, which is available from Magrabar Chemical Corp.; Magrabar PGE-40L®, which is available from Magrabar Chemical Corp.; Magrabar PGE-40T®, which is available from Magrabar Chemical Corp.; Magrabar PGE-42-0®, which is available from Magrabar Chemical Corp.; Magrabar PGE-42L®, which is available from Magrabar Chemical Corp.; Magrabar PGE-42T®, which is available from Magrabar Chemical Corp.; Magrabar PGE-60-0®, which is available from Magrabar Chemical Corp.; Magrabar PGE-60L®, which is available from Magrabar Chemical Corp.; Magrabar PGE-60T®, which is available from Magrabar Chemical Corp.; Magrabar PGE-62-0®, which is available from Magrabar Chemical Corp.; Magrabar PGE-62L®, which is available from Magrabar Chemical Corp.; Magrabar PGE-62T®, which is available from Magrabar Chemical Corp.; Mapeg S-40K®, which is available from BASF Corp.; Marlowet OTS®, which is available from Sasol North America Inc.; Naturechem PGR®, which is available from CasChem®, Inc.; PG No. 4®, which is available from Hart Chemical Corp.; Renex 20®, which is available from Uniqema; Ritox 52®, which is available from RITA Corp.; Ritox 53®, which is available from RITA Corp.; Ritox 59®, which is available from RITA Corp.; Surfax 8916/A®, which is available from Houghton International Inc.; Tego Acid S 40 P®, which is available from Goldschmidt Chemical Corp.; Tego Acid S 100 P®, which is available from Goldschmidt Chemical Corp.; Tween 20®, which is available from Uniqema; Volpo 131®, which is available from Croda Inc.; Alkamuls 400-MO/E®; DeThox Acid O-14®; DeThox Acid 0-16®; DeThox Acid O-9®; DeThox Acid TO-14®; DeThox Acid TO-16.5®; DeThox Acid TO-8.5®; Emerest 2704®; Emerest 2712®; Emerest 2715®; Ethox MA-8®; Ethox MI-14®; Ethox ML-14®; Ethox ML-5®; Ethox MO-14®; Ethox MO-9®; Ethox MS-14®; Ethox MS-23®; Ethox MS-40®; Ethox MS-8®; Ethox TO-16®; Ethox TO-8®; Flexricin 13®; Flexricin 15®; Genapol 1261®; Lumulse 40-O K®; Lumulse 42-O K®; Lumulse GMT-40®; Lumulse PEG 1450®; Lumulse PEG 1450 NF®; Lumulse PEG 8000®; Lumulse PGO®; Lumulse POE (2) Oleyl Amine®; Magrabar PGO-104®; Mapeg 200 ML®; Mapeg 400 MO®; Mapeg 400 MOT®; Mapeg 400DO®; Mapeg 400DOT®; Mapeg 600DOT®; Marlox FK 86®; Marlox MO 154®; Surfonic L12-3®; Surfonic L12-6®; Surfonic L12-8®; Surfonic L24-12®; Surfonic L24-2®; Surfonic L24-22®; Surfonic L24-3®; Surfonic L24-4®; Surfonic L24-5®; Surfonic L24-7®; Surfonic L24-7.1®; Surfonic L24-9®; Surfonic LF-17®; Surfonic LF-18®; Surfonic LF-37®; Surfonic LF-41®; Surfonic LF-42®; Surfonic LF-47®; Surfonic LF-68®; Surfonic P1®; Surfonic P3®; Surfonic P5®; and Surfonic P6®.

Ethoxylated Fatty Esters or Oils (Animal & Veg.), including, but not limited to:

Acconon 6-C10®, which is available from Abitec Corporation; Acconon CC-6®, which is available from Abitec Corporation; Acconon CO-7®, which is available from Abitec Corporation; Aldosperse 40/60 FG®, which is available from Lonza Inc.; Aldosperse ML-23®, which is available from Lonza Inc.; Aldosperse MS-20 FG®, which is available from Lonza Inc.; Alkamuls EL-620®, which is available from Rhodia, Inc.; Alkamuls EL-719®, which is available from Rhodia, Inc.; Alkamuls EL-985®, which is available from Rhodia, Inc.; Arlatone G®, which is available from Uniqema; Arlatone T®, which is available from Uniqema; Atlas G-1045A®, which is available from Uniqema; Atlas G-1086®, which is available from Uniqema; Atlas G-1087®, which is available from Uniqema; Atlas G-1089®, which is available from Uniqema; Atlas G-1096®, which is available from Uniqema; Atlas G-1292®, which is available from Uniqema; Atlas G-1293®, which is available from Uniqema; Atlas G-1300®, which is available from Uniqema; Atlas G-7076®, which is available from Uniqema; Capmul EMG®, which is available from Abitec Corporation; Chemonic CO-40®, which is available from Chemron Corp.; Chemonic LI-3®, which is available from Chemron Corp.; Chemonic LI-7®, which is available from Chemron Corp.; Cirrasol GM®, which is available from Uniqema; Cremophor CO 40®, which is available from BASF Corp.; Cremophor CO 410®, which is available from BASF Corp.; Cremophor EL®, which is available from BASF Corp.; Cremophor GC7®, which is available from BASF Corp.; Cremophor RH-40®, which is available from BASF Corp.; Crovol A-40®, which is available from Croda Inc.; Crovol A-70®, which is available from Croda Inc.; Crovol M-70®, which is available from Croda Inc.; Crovol PK-70®, which is available from Croda Inc.; Cutina E-24®, which is available from Cognis Canada Corp.; Dacospin 12-R®, which is available from Cognis Corporation; Dehymuls HRE-7®, which is available from Cognis Corporation; DeSonic 30C®, which is available from Crompton Corp.; DeSonic 36C®, which is available from Crompton Corp.; DeSonic 40C®, which is available from Crompton Corp.; Durfax 60®, which is available from Loders Croklaan U.S.A.; Durfax 65®, which is available from Loders Croklaan U.S.A.; Durfax 80®, which is available from Loders Croklaan U.S.A.; Durfax EOM®, which is available from Loders Croklaan U.S.A.; Eccoterge NF-2®, which is available from Eastern Color & Chemical Co.; Emulpon CO-360®, which is available from Akzo Nobel Surface Chemistry LLC; Emulpon CO-550®, which is available from Akzo Nobel Surface Chemistry LLC; Emulsogen EL®, which is available from Clariant Corporation; Emulsogen HCO 040®, which is available from Clariant Corporation; Emulsogen HCO 060®, which is available from Clariant Corporation; Emulsynt 1055®, which is available from International Specialty Products/IS; Ethox 3095®, which is available from Ethox Chemicals, LLC; Eumulgin RO-40®, which is available from Cognis Canada Corp.; Genapol G-260®, which is available from Clariant Corporation; Glycosperse L-20®, which is available from Lonza Inc.; Glycosperse O-5®, which is available from Lonza Inc.; Glycosperse O-20®, which is available from Lonza Inc.; Glycosperse O-20 FG®, which is available from Lonza Inc.; Glycosperse S-20®, which is available from Lonza Inc.; Glycosperse S-20 FG®, which is available from Lonza Inc.; Glycosperse TS-20®, which is available from Lonza Inc.; Glycosperse TS-20 FG®, which is available from Lonza Inc.;

Hetan SL®, which is available from Global-Seven, Inc.; Hetan SO®, which is available from Global-Seven, Inc.; Hetan SS®, which is available from Global-Seven, Inc.; Hetoxide C-2®, which is available from Global-Seven, Inc.; Hetoxide C-9®, which is available from Global-Seven, Inc.; Hetoxide C-15®, which is available from Global-Seven, Inc.; Hetoxide C-25®, which is available from Global-Seven, Inc.; Hetoxide C-40®, which is available from Global-Seven, Inc.; Hetoxide C-200®, which is available from Global-Seven, Inc.; Hetoxide C-200-50%®, which is available from Global-Seven, Inc.; Hetoxide GC-30®, which is available from Global-Seven, Inc.; Hetoxide HC-60®, which is available from Global-Seven, Inc.; Ice No. 2®, which is available from Loders Croklaan U.S.A.; Incrocas 30/40®, which is available from Croda Inc.; Lexol EC®, which is available from Inolex Chemical Co.; Lexol EO®, which is available from Inolex Chemical Co.; Lipocol HCO-40®, which is available from Lipo Chemicals, Inc.; Lipocol HCO-60®, which is available from Lipo Chemicals, Inc.; Lipocol O-3 Special®, which is available from Lipo Chemicals, Inc.; Lipopeg 2-L®, which is available from Lipo Chemicals, Inc.; Lipopeg 4-DO®, which is available from Lipo Chemicals, Inc.; Lipopeg 4-DS®, which is available from Lipo Chemicals, Inc.; Lipovol GTB®, which is available from Lipo Chemicals, Inc.; Lonzest SML-20®, which is available from Lonza Inc.; Lonzest SMO-20®, which is available from Lonza Inc.; Lonzest SMS-20®, which is available from Lonza Inc.; Lonzest STO-20®, which is available from Lonza Inc.; Lonzest STS-20®, which is available from Lonza Inc.; Lumulse GR-40®, which is available from Lambent Technologies Corp.; Lumulse GRH-40®, which is available from Lambent Technologies Corp.; Lumulse POE (7) GML®, which is available from Lambent Technologies Corp.; Lumulse POE (12) Glyc®, which is available from Lambent Technologies Corp.; Lumulse POE (40) MS KP®, which is available from Lambent Technologies Corp.; Marlowet 4750®, which is available from Sasol North America Inc.; Marlowet LVS®, which is available from Sasol North America Inc.; Marlowet R 11®, which is available from Sasol North America Inc.; Marlowet R 40®, which is available from Sasol North America Inc.; Mazol 80 MGK®, which is available from BASF Corp.; Nonionic Emulsifier T-9®, which is available from Werner G. Smith Inc.; Oronal LCG®, which is available from Seppic Inc.; Polyderm PPI-CO-200®, which is available from Alzo International, Inc.; Polyderm PPI-CO-40®, which is available from Alzo International, Inc.; Rewoderm LI 520-70®, which is available from Goldschmidt Chemical Corp.; Ritapeg 150 DS®, which is available from RITA Corp.; Softigen 767®, which is available from Sasol North America Inc.; Surfactol 318®, which is available from CasChem®, Inc.; Surfactol 365®, which is available from CasChem®, Inc.; Syn Lube 107®, which is available from Milliken Chemical; Syn Lube 728®, which is available from Milliken Chemical; Syn Lube 1632H®, which is available from Milliken Chemical; Syn Lube 6277-A®, which is available from Milliken Chemical; T-Det C-20®, which is available from Harcros Chemicals Inc.; T-Det C-40®, which is available from Harcros Chemicals Inc.; Tally 100 Plus®, which is available from Loders Croklaan U.S.A.; Uniperol EL®, which is available from BASF Corp.; Acconon E®; Chemax CO-16®; Chemax CO-200/50®; Chemax CO-25®; Chemax CO-30®; Chemax CO-36®; Chemax CO-40®; Chemax CO-5®; Chemax CO-80®; Chemax DNP-150/50®; Chemax DNP-18®; Chemax DNP-8®; Chemax E 200 ML®; Chemax E 200 MO®; Chemax E 400 ML®; Chemax E 400 MO®; Chemax E 600 ML®; Chemax E 600 MO®; Chemax E1000 MO®; Chemax E1000 MS®; Chemax E200 MS®; Chemax E400 MS®; Chemax E600 MS®; Chemax HCO-16®; Chemax HCO-200/50®; Chemax HCO-25®; Chemax HCO-5®; Chemax TO-16®; Chemax TO-8®; Colalube 3409®; Colalube 3411®; Colalube 3413®; Colalube 3414®; Colalube 3415®; Colalube 3416®; Colalube 3417®; DePeg 16-CO®; DePeg 25-CO®; DePeg 30-CO®; DePeg 40-CO®; DePeg 5-CO®; DePeg 80-CO®; Ethox 3095®; Ethox CO-16®; Ethox CO-200®; Ethox CO-25®; Ethox CO-30®; Ethox CO-36®; Ethox CO-40®; Ethox CO-5®; Hetoxide BN-13®; Hetoxide DNP-4®; Hetoxide DNP-9.6®; Hetoxide G-26®; Hetoxide G-7®; Hetoxide GT-20®; Hetoxide HC-40®; Lipo GMS 450®; Lipo Polyglycol 1000®; Lipo Polyglycol 200®; Lipo Polyglycol 300®; Lipo Polyglycol 3350®; Lipo Polyglycol 400®; Lipo Polyglycol 600®; Surfonic CO-15®; Surfonic CO-25®; Surfonic CO-30®; Surfonic CO-36®; Surfonic CO-42®; Surfonic TX-CCN®; Tagat CH 40®; Tagat CH 60®; Tagat L 2®; Tagat S®; Tagat S 2®; and Tally 100 Plus®.

Fatty Esters, including but not limited to,

Actralube-Syn 147®, which is available from Georgia-Pacific Corp.; Atlas G-1556°, which is available from Uniqema; Atlas G-1564°, which is available from Uniqema; Atlasol Base Oil S®, which is available from Atlas Refinery Inc.; Base ML®, which is available from Keil Chemical; Base MT®, which is available from Keil Chemical; Cerasynt 303®, which is available from International Specialty Products/IS; Dermol 1012®, which is available from Alzo International, Inc.; Kemester 4000®, which is available from Crompton Corp.; Lactipol S®, which is available from Canamex Quimicos S.A de C.v; Magrabar PGO®, which is available from Magrabar Chemical Corp.; Mayco Base BFO®, which is available from Dover Chemical Corp.; Methyl Linoleate®, which is available from Hart Chemical Corp.; Pationic 122A°, which is available from RITA Corp.; Pationic 138C®, which is available from RITA Corp.; Pationic CSC, which is available from RITA Corp.; Pationic ISC, which is available from RITA Corp.; Pationic SBC, which is available from RITA Corp.; Pationic SSC, which is available from RITA Corp.; Ritasor, which is available from RITA Corp.; Tego Alkanol CS 20®, which is available from Goldschmidt Chemical Corp.; Tego Alkanol L23 P®, which is available from Goldschmidt Chemical Corp.; Tego Alkanol 52®, which is available from Goldschmidt Chemical Corp.; Tego Alkanol S20 ®, which is available from Goldschmidt Chemical Corp.; Triemulsifier 600 MS®, which is available from Tri-Tex Co.®, Inc.; Santone 10-10-0®; Santone 3-1-S XTR®; Santone 3-1-SH®; and Santone 8-1-O®.

Glycerol Esters, including but not limited to:

Agro #9 Wint SBO®, which is available from Lambent Technologies Corp.; Ahcovel Base 700®, which is available from Uniqema; Aldo HMS FG®, which is available from Lonza Inc.; Aldo MLD®, which is available from Lonza Inc.; Aldo MLD FG®, which is available from Lonza Inc.; Aldo MO FG®, which is available from Lonza Inc.; Aldo MS®, which is available from Lonza Inc.; Aldo MS FG®, which is available from Lonza Inc.; Aldo MS LG FG®, which is available from Lonza Inc.; Aldo MSD®, which is available from Lonza Inc.; Aldo MSD FG®, which is available from Lonza Inc.; Aldosperse O-20 FG®, which is available from Lonza Inc.; Aldosperse TS-20 FG®, which is available from Lonza Inc.; Aldosperse TS-40 FG®, which is available from Lonza Inc.; Arlacel 165®, which is available from Uniqema; Arlacel 186®, which is available from Uniqema; Capmul GMO®, which is available from Abitec Corporation; Capmul GMS®, which is available from Abitec Corporation; Caprol 3GO®, which is available from Abitec Corporation; Caprol 3GVS®, which is available from Abitec Corporation; Caprol 6G2S®, which is available from Abitec Corporation; Caprol 10G40®, which is available from Abitec Corporation; Caprol 10G100®, which is available from Abitec Corporation; Caprol ET®, which is available from Abitec Corporation; Caprol PGE860®, which is available from Abitec Corporation; Cerasynt 945®, which is available from International Specialty Products/IS; Cerasynt GMS®, which is available from International Specialty Products/IS; Cerasynt Q®, which is available from International Specialty Products/IS; Cerasynt SD®, which is available from International Specialty Products/IS; Cerasynt WM®, which is available from International Specialty Products/IS; Chemsperse 14®, which is available from Chemron Corp.; Cremophor GO-32®, which is available from BASF Corp.; Cremophor GS11®, which is available from BASF Corp.; Cremophor GS-32®, which is available from BASF Corp.; Cutina KD-16®, which is available from Cognis Canada Corp.; Dehymuls PGPH®, which is available from Cognis Corporation; Dermol DGDIS®, which is available from Alzo International, Inc.; Dermol DGMIS®, which is available from Alzo International, Inc.; Dermol G-76®, which is available from Alzo International, Inc.; Dermol G-7DI®, which is available from Alzo International, Inc.; Dermol NGDI®, which is available from Alzo International, Inc.; Dermolan GLH®, which is available from Alzo International, Inc.; Drewmulse GMO®, which is available from Stepan Company; Drewpol 3-5-M®, which is available from Stepan Company; Durlac 100 W®, which is available from Loders Croklaan U.S.A.; Dur-Lo®, which is available from Loders Croklaan U.S.A.; Dynasan 118®, which is available from Sasol North America Inc.; EC-25®, which is available from Loders Croklaan U.S.A.; EM 40®, which is available from Keil Chemical; Emerest 2400®, which is available from Cognis Corporation; Emerest 2452®, which is available from Cognis Corporation; Empilan G-26®, which is available from Huntsman LLC; Genapol TSM®, which is available from Clariant Corporation; Hostacerin DGI®, which is available from Clariant Corporation; Hostacerin DGL®, which is available from Clariant Corporation; Hostacerin DGMS®, which is available from Clariant Corporation; Hostacerin DGSB®, which is available from Clariant Corporation; Ice No. 2®, which is available from Loders Croklaan U.S.A.; Imwitor 742®, which is available from Sasol North America Inc.; Imwitor 780 K®, which is available from Sasol North America Inc.; Imwitor 960 Flakes®, which is available from Sasol North America Inc.; Isolan GI 34®, which is available from Goldschmidt Chemical Corp.; Isolan GO 33®, which is available from Goldschmidt Chemical Corp.; Kemester 1000®, which is available from Crompton Corp.; Kemester 2000®, which is available from Crompton; Kemester 2000®, which is available from Crompton Corp.; Kemester 6000SE®, which is available from Crompton Corp.; Lamecreme DGE 18®, which is available from Cognis Corporation; Lexemul 515®, which is available from Inolex Chemical Co.; Lexemul 561®, which is available from Inolex Chemical Co.; Lexemul AR®, which is available from Inolex Chemical Co.; Lexemul AS®, which is available from Inolex Chemical Co.; Lexemul GDL®, which is available from Inolex Chemical Co.; Lexemul T®, which is available from Inolex Chemical Co.; Lipomulse 165®, which is available from Lipo Chemicals, Inc.; Lumulse GML K®, which is available from Lambent Technologies Corp.; Lumulse GMO K®, which is available from Lambent Technologies Corp.; Lumulse GMR K®, which is available from Lambent Technologies Corp.; Lumulse GMT K®, which is available from Lambent Technologies Corp.; Magrabar GMC®, which is available from Magrabar Chemical Corp.; Magrabar GMO-CK®, which is available from Magrabar Chemical Corp.; Magrabar MDG-5050®, which is available from Magrabar Chemical Corp.; Magrabar PGO-315®, which is available from Magrabar Chemical Corp.; Magrabar PGO-1010®, which is available from Magrabar Chemical Corp.; Mazol 300K®, which is available from BASF Corp.; Mazol GMO-K®, which is available from BASF Corp.; Mazol GMS-K®, which is available from BASF Corp.; Mazol PG031-K®, which is available from BASF Corp.; Miglyol 812®, which is available from Sasol North America Inc.; Norfox 165C®, which is available from Norman, Fox & Co.; Schercemol GMIS®, which is available from Noveon®, Inc.; Tegin®, which is available from Goldschmidt Chemical Corp.; Tegin 4100 Pellets®, which is available from Goldschmidt Chemical Corp.; Tegin M Pellets®, which is available from Goldschmidt Chemical Corp.; Tegin OV®, which is available from Goldschmidt Chemical Corp.; Teginacid H®, which is available from Goldschmidt Chemical Corp.; Tego Cosmo P813®, which is available from Goldschmidt Chemical Corp.; Wickenol 535®, which is available from Alzo International, Inc.; Witconol 14®, which is available from Akzo Nobel Surface Chemistry LLC; Witconol 14®, which is available from Crompton Corp.; Witconol 14F®, which is available from Crompton Corp.; Witconol 18L®, which is available from Crompton Corp.; Witconol GOT®, which is available from Crompton Corp.; Witconol MST®, which is available from Crompton Corp.; Witconol RHT®, which is available from Crompton Corp.; Alkamuls 400-DO®; Dur-Em 114®; Dur-Em 117®; Dur-Em 204®; Dur-Em 207®; Dur-Em 207E®; Glicepol 160®; Glicepol 560®; Glicepol GMS 20®; Polyaldo 10-2-P®; Polyaldo DGDO®; Polyaldo HGDS®; Polyaldo TGMS®; Surfonic E400-MO®; and Tegin®.

Glycol Esters, including, but not limited to:

Alkamuls 600 DO®, which is available from Rhodia, Inc.; Alkamuls SEG®, which is available from Rhodia, Inc.; Atlas EM-2®, which is available from Atlas Refinery Inc.; Cerasynt IP®, which is available from International Specialty Products/IS; Cerasynt M®, which is available from International Specialty Products/IS; Cerasynt MN®, which is available from International Specialty Products/IS; Cerasynt PA®, which is available from International Specialty Products/IS; Chemsperse EGDS®, which is available from Chemron Corp.; Chemsperse EGMS®, which is available from Chemron Corp.; Colonial Monolaurin®, which is available from Colonial Chemical Co.; DeMuls SGE-95®, which is available from DeForest Enterprises, Inc.; Eccoterge 200®, which is available from Eastern Color & Chemical Co.; Emerest 2380®, which is available from Cognis Corporation; Ethox 2610®, which is available from Ethox Chemicals, LLC; Ethox DO-9®, which is available from Ethox Chemicals, LLC; Ethox DO-14®, which is available from Ethox Chemicals, LLC; Ethox SO-9®, which is available from Ethox Chemicals, LLC; Fizul MD-318®, which is available from Finetex Inc.; Genapol EGDS-VHP®, which is available from Clariant Corporation; Genapol TS Powder®, which is available from Clariant Corporation; Hostacerin WO®, which is available from Clariant Corporation; Inversol 140®, which is available from Keil Chemical; Kemester 104®, which is available from Crompton Corp.; Kemester 205®, which is available from Crompton Corp.; Kemester 226®, which is available from Crompton Corp.; Kemester 5221 SE®, which is available from Crompton Corp.; Kemester EGDS®, which is available from Crompton Corp.; Lexemul EGDS®, which is available from Inolex Chemical Co.; Lexemul EGMS®, which is available from Inolex Chemical Co.; Lexemul P®, which is available from Inolex Chemical Co.; Lipo DGLS®, Self-Emulsifying®, which is available from Lipo Chemicals, Inc.; Lipo EGDS®, which is available from Lipo Chemicals, Inc.; Lipo PGMS®, which is available from Lipo Chemicals, Inc.; Liposorb S-4®, which is available from Lipo Chemicals, Inc.; Liposorb TO-20®, which is available from Lipo Chemicals, Inc.; Lumulse PGO®, which is available from Lambent Technologies Corp.; Mackester EGDS®, which is available from The McIntyre Group; Mackester EGMS®, which is available from The McIntyre Group; Mackester GSTP®, which is available from The McIntyre Group; Mackester Series®, which is available from The McIntyre Group; Magrabar PDG-50®, which is available from Magrabar Chemical Corp.; Mapeg 6000 DS®, which is available from BASF Corp.; Marlowet 4702®, which is available from Sasol North America Inc.; Monalube 305®, which is available from Uniqema; Monalube 310®, which is available from Uniqema; Monalube 315®, which is available from Uniqema; Monalube 320®, which is available from Uniqema; Monalube 325®, which is available from Uniqema; Monalube 330®, which is available from Uniqema; Naturechem PGHS®, which is available from CasChem®, Inc.; Polycastorol PLO-840®, which is available from Magrabar Chemical Corp.; Polytex 10M®, which is available from Lipo Chemicals, Inc.; Ritasynt IP®, which is available from RITA Corp.; Ross Chem PEG 600 DT®, which is available from Lubrizol Foam Control Additives; Schercemol PGMS®, which is available from Noveon®, Inc.; Sponto H-44C®, which is available from Crompton Corp.; Tegin G®, which is available from Goldschmidt Chemical Corp.; Witbreak DGE-182®, which is available from Akzo Nobel Surface Chemistry LLC; Witbreak DGE-182®, which is available from Crompton Corp.; Witbreak DRA-21®, which is available from Akzo Nobel Surface Chemistry LLC; Witbreak DRA-21®, which is available from Crompton Corp.; Witbreak DRA-50®, which is available from Akzo Nobel Surface Chemistry LLC; Witbreak DRA-50®, which is available from Crompton Corp.; Witconol F26-46®, which is available from Crompton Corp.; Witconol H-32®, which is available from Akzo Nobel Surface Chemistry LLC; Witconol H-33®, which is available from Akzo Nobel Surface Chemistry LLC; Witconol H-35A®, which is available from Crompton Corp.; Witconol RHP®, which is available from Crompton Corp.; Ethox DO-14®; Ethox DO-9®; Pegosperse 100-L®; Pegosperse 100-O®; Pegosperse 100-S®; Pegosperse 1500-MS®; Pegosperse 1750-MS®; Pegosperse 200 DL®; Pegosperse 200-ML®; Pegosperse 400-DL®; Pegosperse 400-DO®; Pegosperse 400-DS®; Pegosperse 400-ML®; Pegosperse 400-MO®; Pegosperse 400-MOT®; Pegosperse 400-MS®; Pegosperse 50-DS®; Pegosperse 50-MS®; Pegosperse 600-ML®; Pegosperse 600-MS®; Protegin V®; Protegin W®; Protegin WX®; and Protegin XV®.

Lanolin-based Derivatives, including, but not limited to,

Amerchol CAB®, which is available from Amerchol Corp.; Amerchol L-101®, which is available from Amerchol Corp.; Amerlate LFA-LO®, which is available from Amerchol Corp.; Amerlate P®, which is available from Amerchol Corp.; Barre Common Degras®, which is available from RITA Corp.; Cholesterol NF®, which is available from Croda Inc.; Crodalan AWS®, which is available from Croda Inc.; Crodalan LA®, which is available from Croda Inc.; Emery 1650®, which is available from Cognis Canada Corp.; Emery 1650®, which is available from Cognis Corporation; Emery 1740®, which is available from Cognis Canada Corp.; Emery 1740®, which is available from Cognis Corporation; Forlan 500®, which is available from RITA Corp.; Forlan L®, which is available from RITA Corp.; Laneto 50®, which is available from RITA Corp.; Laneto 100®, which is available from RITA Corp.; Laneto AWS®, which is available from RITA Corp.; Lanfrax 1776®, which is available from Cognis Canada Corp.; Lanfrax 1776®, which is available from Cognis Corporation; Lanogel 21®, which is available from Amerchol Corp.; Lipolan®, which is available from Lipo Chemicals, Inc.; Lipolan 31®, which is available from Lipo Chemicals, Inc.; OHlan®, which is available from Amerchol Corp.; Polychol 5®, which is available from Croda Inc.; Polychol 15®, which is available from Croda Inc.; Ritacetyl®, which is available from RITA Corp.; Ritachol®, which is available from RITA Corp.; Ritahydrox®, which is available from RITA Corp.; Ritalafa®, which is available from RITA Corp.; Ritalan®, which is available from RITA Corp.; Ritalan AWS®, which is available from RITA Corp.; Ritalan C®, which is available from RITA Corp.; Ritawax®, which is available from RITA Corp.; Ritawax AEO®, which is available from RITA Corp.; Ritawax ALA®, which is available from RITA Corp.; Solan/Solan 50/Super Solan®, which is available from Croda Inc.; Super Hartolan/Hartolan®, which is available from Croda Inc.; Supersat AWS-4®, which is available from RITA Corp.; and Supersat AWS-24®, which is available from RITA Corp.; Lecithin and Lecithin Derivatives, including but not limited to, Alcolec®, which is available from American Lecithin Co.; Lecithin®, which is available from Archer Daniels Midland Company; Lexin K®, which is available from American Lecithin Co.; and Natipide®, which is available from American Lecithin Co.

Lignin and Lignin Derivatives, including but not limited to:

Diwatex XP 9®, which is available from Borregaard Lignotech USA Inc.; Dynasperse LCD®, which is available from Borregaard Lignotech USA Inc.; Indulin SAL®, which is available from MeadWestvaco Corp.; Indulin W-1®, which is available from MeadWestvaco Corp.; Indulin W-5®, which is available from MeadWestvaco Corp.; Lignosol FTA®, which is available from Borregaard Lignotech USA Inc.; Lignosol SFX-65®, which is available from Borregaard Lignotech USA Inc.; Marasperse 52 CP®, which is available from Borregaard Lignotech USA Inc.; Marasperse AG®, which is available from Borregaard Lignotech USA Inc.; Marasperse CBOS-4®, which is available from Borregaard Lignotech USA Inc.; and, Ufoxane 2®, which is available from Borregaard Lignotech USA Inc.

Methyl Esters, including, but not limited to:

E.B. Cleaner AK®, which is available from Eastern Color & Chemical Co.; Oleocal ME-70®, which is available from Lambent Technologies Corp.; Oleocal ME-92®, which is available from Lambent Technologies Corp.; Oleocal ME-112®, which is available from Lambent Technologies Corp.; and Oleocal ME-130®, which is available from Lambent Technologies Corp.

Monoglycerides and Derivatives, including but not limited to:

Dynacet 211®, which is available from Sasol North America Inc.; Hetsorb S-20®, which is available from Global-Seven, Inc.; Imwitor 191®, which is available from Sasol North America Inc.; Imwitor 370®, which is available from Sasol North America Inc.; Imwitor 375®, which is available from Sasol North America Inc.; Imwitor 900®, which is available from Sasol North America Inc.; Imwitor 945®, which is available from Sasol North America Inc.; Imwitor 2020®, which is available from Sasol North America Inc.; Kemester 5500®, which is available from Crompton Corp.; Kemester 6000®, which is available from Crompton Corp.; Magrabar GMC®, which is available from Magrabar Chemical Corp.; Magrabar GMO-CK®, which is available from Magrabar Chemical Corp.; Magrabar GPC-10®, which is available from Magrabar Chemical Corp.; Magrabar MDG-5050®, which is available from Magrabar Chemical Corp.;

Monalube 335®, which is available from Uniqema; Monoglycerides Glyceryl Monostearate Archer Daniels Midland Company; Rita GMS®, which is available from RITA Corp.; Ritamulse SCG®, which is available from RITA Corp.; Softigen 701®, which is available from Sasol North America Inc.; and Tally 100 Plus®, which is available from Loders Croklaan U.S.A.

Polyethylene Glycols, including, but not limited to:

Emulgade PL 68/50®, which is available from Cognis Corporation; Lumulse PEG®, which is available from Lambent Technologies Corp.; Rhodasurf PEG-400®, which is available from Rhodia, Inc.; Rhodasurf PEG-600®, which is available from Rhodia, Inc.; and Witconol PEG-400®, which is available from Akzo Nobel Surface Chemistry LLC.

Polymeric Surfactants, including, but not limited to:

Acritamer PNC-EG®, which is available from RITA Corp.; Ag-Rho DEP-775®, which is available from Rhodia, Inc.; APG 325N Glycoside®, which is available from Cognis Corporation; Aristoflex AVC®, which is available from Clariant Corporation; Aristoflex HMB®, which is available from Clariant Corporation; Burco NPS-225®, which is available from Burlington Chemical Co.®, Inc.; Burco NPS-816®, which is available from Burlington Chemical Co.®, Inc.; Chemccinate 5603®, which is available from Chemron Corp.; Cosmedia Guar C-261 N®, which is available from Cognis Corporation; Gantrez S-95®, which is available from International Specialty Products/IS; Glucopon 220 UP®, which is available from Cognis Corporation; Glucopon 225 DK®, which is available from Cognis Corporation; Glucopon 425 N®, which is available from Cognis Corporation; Glucopon 600 UP®, which is available from Cognis Corporation; Glucopon 625 UP®, which is available from Cognis Corporation; Pemulen 1621®, which is available from Noveon®, Inc.; Pemulen 1622®, which is available from Noveon®, Inc.; Pemulen TR-1®, which is available from Noveon®, Inc.; Pemulen TR-2®, which is available from Noveon®, Inc.; Plantacare 818®, which is available from Cognis Corporation; Plantapon LGC Sorb®, which is available from Cognis Corporation; Plantaren 1200N®, which is available from Cognis Corporation; Plantaren 2000N®, which is available from Cognis Corporation; Viscolam AT 64®, which is available from RITA Corp.; Viscolam AT 64P®, which is available from RITA Corp.; Viscolam AT 100®, which is available from RITA Corp.; Viscolam MAC 7®, which is available from RITA Corp.; Viscolam SMC 20®, which is available from RITA Corp.; Witbreak RTC-323®, which is available from Crompton Corp.; and WSI 3700®, which is available from Jacam Chemicals, L.L.C.

Propoxylated & Ethoxylated Fatty Acids, Alcohols, or Alkyl Phenols, including but not limited to:

Antarox AA-60®, which is available from Rhodia, Inc.; Antarox LF-224®, which is available from Rhodia, Inc.; Burcomul DFE-45®, which is available from Burlington Chemical Co.®, Inc.; Burcoterge LFE-1000®, which is available from Burlington Chemical Co.®, Inc.; Chemal LF-25B®, which is available from Chemax Performance Solutions; Chemal LF-40B®, which is available from Chemax Performance Solutions; Dehypon LS-36®, which is available from Cognis Canada Corp.; Dehypon LS-36®, which is available from Cognis Corporation; Dehypon LS-54®, which is available from Cognis Canada Corp.; Dehypon LS-54®, which is available from Cognis Corporation; Delonic 100 VLF®, which is available from DeForest Enterprises, Inc.; Delonic LF-60 MOD®, which is available from DeForest Enterprises, Inc.; Epiderm B®, which is available from Huntsman LLC; Ethylan 1206®, which is available from Akzo Nobel Surface Chemistry LLC; Ethylan NS-500K®, which is available from Akzo Nobel Surface Chemistry LLC; Ethylan NS-500LQ®, which is available from Akzo Nobel Surface Chemistry LLC; Genapol 1392®, which is available from Clariant Corporation; Genapol 2317®, which is available from Clariant Corporation; Genapol 26EP710®, which is available from Clariant Corporation; Genapol EP 1022®, which is available from Clariant Corporation; Genapol EP 1024®, which is available from Clariant Corporation; Genapol EP 6068®, which is available from Clariant Corporation; Genapol NP915®, which is available from Clariant Corporation; Kieralon MFB®, which is available from BASF Corp.; Lumisolve CSA-80 V®, which is available from Lambent Technologies Corp.; Marlowet 5001®, which is available from Sasol North America Inc.; Marlox FK 64®, which is available from Sasol North America Inc.; Marlox MO 124®, which is available from Sasol North America Inc.; Marlox S 58®, which is available from Sasol North America Inc.; Nonatell 1003®, which is available from Tomah Products®, Inc.; Nonatell 1038®, which is available from Tomah Products®, Inc.; Nonatell 1052®, which is available from Tomah Products®, Inc.; Nonatell 1061®, which is available from Tomah Products®, Inc.; Nonatell 1075®, which is available from Tomah Products®, Inc.; Nonatell 1088®, which is available from Tomah Products®, Inc.; Nonatell 1123®, which is available from Tomah Products®, Inc.; Nonatell 1153®, which is available from Tomah Products®, Inc.; Nonatell 1161®, which is available from Tomah Products®, Inc.; Nonatell 1172®, which is available from Tomah Products®, Inc.; Nonatell 1181®, which is available from Tomah Products®, Inc.; Norfox 36®, which is available from Norman, Fox & Co.; Procetyl AWS®, which is available from Croda Inc.; Sandoxylate SX 412®Liquid, which is available from Clariant Corporation; Sandoxylate SX 418®, hich is available from Clariant Corporation; Surfonic JL-80X®, which is available from Huntsman LLC; Surfonic JL-80X-B1®, which is available from Huntsman LLC; Surfonic L4-29X®, which is available from Huntsman LLC; Surfonic LF®, which is available from Huntsman LLC; T-Det A826®, which is available from Harcros Chemicals Inc.; T-Det LF-416®, which is available from Harcros Chemicals Inc.; Tergitol Min-Foam 1X®, which is available from Dow Chemical Company; Tergitol Min-Foam 2X®, which is available from Dow Chemical Company; Triton CF-21®, which is available from Dow Chemical Company; Triton CF-76®, which is available from Dow Chemical Company; Triton XL-80N®, which is available from Dow Chemical Company; Witconol NS-98®, which is available from Akzo Nobel Surface Chemistry LLC; Witconol NS-108LQ®, which is available from Akzo Nobel Surface Chemistry LLC; Witconol NS-145®, which is available from Akzo Nobel Surface Chemistry LLC; Witconol NS-179®, which is available from Akzo Nobel Surface Chemistry LLC; Chemal LFL-17®; Chemal LFL-19®; Chemal LFL-28 C®; Chemal LFL-47®; Delonic LF-EP-15®; Delonic LF-EP-18®; Delonic LF-EP-20®; Delonic LF-EP-25®; Delonic LF-EP-30®; Delonic LF-EP-35®; Delonic LF-EP-40®; Delonic LF-EP-61®; and, Soprophor 796/P®.

Protein-based Surfactants, including, but not limited to:

AminoFoam W®, which is available from Croda Inc.; Amiter LGOD-2®, which is available from Ajinomoto USA, Inc.; Amiter LGS-2®, which is available from Ajinomoto USA, Inc.; Amiter LGS-5®, which is available from Ajinomoto USA, Inc.; Lamepon S®, which is available from Cognis Canada Corp.; Lamepon S®, which is available from Cognis Corporation; Maypon 4C®, which is available from Inolex Chemical Co.; May-Tein C®, which is available from Maybrook, Inc.; May-Tein CT®, which is available from Maybrook, Inc.; May-Tein KTS®, which is available from Maybrook, Inc.; May-Tein SY®, which is available from Maybrook, Inc.; Plantapon S®, which is available from Cognis Corporation; Proteol APL®, which is available from Seppic Inc.; Proteol OAT®, which is available from Seppic Inc.; Pyroter CPI-40®, which is available from Ajinomoto USA, Inc.; Pyroter GPI-25®, which is available from Ajinomoto USA, Inc.; Supro-Tein S®, which is available from Maybrook, Inc.; and Supro-Tein V®, which is available from Maybrook, Inc.; Sarcosine Derivatives, including but not limited to Crodasinic LS-30®, which is available from Croda Inc.; Vanseal CS®, which is available from R. T. Vanderbilt Co. Inc.; Vanseal LS®, which is available from R. T. Vanderbilt Co. Inc.; Vanseal MS®, which is available from R. T. Vanderbilt Co. Inc.; Vanseal NACS-30®, which is available from R. T. Vanderbilt Co. Inc.; Vanseal NALS-95®, which is available from R. T. Vanderbilt Co. Inc.; and Vanseal OS®, which is available from R. T. Vanderbilt Co. Inc.; Silicone-based Surfactants, including but not limited to, Abil-B-9950®, which is available from Goldschmidt Chemical Corp.; Abil Care 85®, which is available from Goldschmidt Chemical Corp.; Abil EM 90®, which is available from Goldschmidt Chemical Corp.; Abil EM 97®, which is available from Goldschmidt Chemical Corp.; Abil WE-09®, which is available from Goldschmidt Chemical Corp.; Dow Corning 1248 Fluid®, which is available from Dow Corning Corp.; Dow Corning 3225C®Formulation Aid, which is available from Dow Corning Corp.; Dow Corning 5200®Formulation Aid, which is available from Dow Corning Corp.; Dow Corning Q4-3667®Fluid, which is available from Dow Corning Corp.; Monasil PCA®, which is available from Uniqema; Monasil PDM®, which is available from Uniqema; Monasil PLN®, which is available from Uniqema; Polyderm PPI-S1-WS®, which is available from Alzo International, Inc.; Troysol 380W®, which is available from Troy Corporation; Troysol 5366®, which is available from Troy Corporation; Abil-B-88183®; Abil-B-8832®; Abil-B-8843®; Abil-B-8851®; Abil-B-8852®; Abil-B-8863®; Dow Corning 190 Surfactant®; Dow Corning 193 Surfactant®; Dow Corning 5103 Surfactant®; Dow Corning FF400 Fluid®; Silwet L-7001®; Silwet L-7002®; Silwet L-7087®; Silwet L-720®; Silwet L-7200®; Silwet L-7210®; Silwet L-722®; Silwet L-7220®; Silwet L-7230®; Silwet L-7500®; Silwet L-7600®; Silwet L-7602®; Silwet L-7604®; Silwet L-7605®; Silwet L-7607®; Silwet L-7608®; Silwet L-7622®; Silwet L-7657®; and Silwet L-77®; Sorbitan Derivatives, including but not limited to, Alkamuls SML®, which is available from Rhodia, Inc.; Alkamuls SMO®, which is available from Rhodia, Inc.; Alkamuls STO®, which is available from Rhodia, Inc.; Arlacel 20®, which is available from Uniqema; Arlacel 40®, which is available from Uniqema; Arlacel 60®, which is available from Uniqema; Arlacel 80®, which is available from Uniqema; Arlacel C®, which is available from Uniqema; Armul 21®, which is available from Crompton Corp.; Atlox 80®, which is available from Uniqema; Atlox 847®, which is available from Uniqema; Atlox 1045A®, which is available from Uniqema; Canarcel 20®, which is available from Canamex Quimicos S.A de C.v; Canarcel 60®, which is available from Canamex Quimicos S.A de C.v; Canarcel 80®, which is available from Canamex Quimicos S.A de C.v; Canarcel TW 20®, which is available from Canamex Quimicos S.A de C.v; Canarcel TW 60®, which is available from Canamex Quimicos S.A de C.v; Canarcel TW 80®, which is available from Canamex Quimicos S.A de C.v; Coladet BSB-P®, which is available from Colonial Chemical Co.; Customulse 0-20®, which is available from Custom Ingredients, Inc.; Dehymuls E®, which is available from Cognis Canada Corp.; DeSotan SMO®, which is available from Crompton Corp.; DeSotan SMO-20®, which is available from Crompton Corp.; DeSotan SMT®, which is available from Crompton Corp.; DeSotan SMT-20®, which is available from Crompton Corp.; Durfax 60®, which is available from Loders Croklaan U.S.A.; Durfax 65®, which is available from Loders Croklaan U.S.A.; Durfax 80®, which is available from Loders Croklaan U.S.A.; Durtan 60®, which is available from Loders Croklaan U.S.A.; Durtan 65®, which is available from Loders Croklaan U.S.A.; Liposorb L®, which is available from Lipo Chemicals, Inc.; Liposorb L-10®, which is available from Lipo Chemicals, Inc.; Liposorb L-20®, which is available from Lipo Chemicals, Inc.; Liposorb O®, which is available from Lipo Chemicals, Inc.; Liposorb 0-20®, which is available from Lipo Chemicals, Inc.; Liposorb P®, which is available from Lipo Chemicals, Inc.; Liposorb P-20®, which is available from Lipo Chemicals, Inc.; Liposorb S®, which is available from Lipo Chemicals, Inc.; Liposorb S-20®, which is available from Lipo Chemicals, Inc.; Liposorb SQO®, which is available from Lipo Chemicals, Inc.; Liposorb TO®, which is available from Lipo Chemicals, Inc.; Liposorb TS®, which is available from Lipo Chemicals, Inc.; Liposorb TS-20®, which is available from Lipo Chemicals, Inc.; Lumisorb PS®, which is available from Lambent Technologies Corp.; Lumisorb SMO (T)®, which is available from Lambent Technologies Corp.; Lumisorb SMS K®, which is available from Lambent Technologies Corp.; Lumisorb SSO®, which is available from Lambent Technologies Corp.; Lumisorb STS K®, which is available from Lambent Technologies Corp.; Lumisorb STT®, which is available from Lambent Technologies Corp.; Magrabar SMO®, which is available from Magrabar Chemical Corp.; Magrabar SMO-VEG®, which is available from Magrabar Chemical Corp.; Magrabar SMT®, which is available from Magrabar Chemical Corp.; Magrabar STO®, which is available from Magrabar Chemical Corp.; Miracare BC-27®, which is available from Rhodia, Inc.; Ritabate 20®, which is available from RITA Corp.; Ritabate 40®, which is available from RITA Corp.; Ritabate 60®, which is available from RITA Corp.; Ritabate 80®, which is available from RITA Corp.; T-Maz®, which is available from BASF Corp.; Tego SML®, which is available from Goldschmidt Chemical Corp.; Tego SML 20®, which is available from Goldschmidt Chemical Corp.; Tego SMO 80 V®, which is available from Goldschmidt Chemical Corp.; Tego SMO V®, which is available from Goldschmidt Chemical Corp.; Tego SMS®, which is available from Goldschmidt Chemical Corp.; Tego STO V®, which is available from Goldschmidt Chemical Corp.; Tween 21®, which is available from Uniqema; Tween 40®, which is available from Uniqema; Tween 60®, which is available from Uniqema; Tween 60 K®, which is available from Uniqema; Tween 61®, which is available from Uniqema; Tween 65®, which is available from Uniqema; Tween 80®, which is available from Uniqema; Tween 80 K®, which is available from Uniqema; Tween 81®, which is available from Uniqema; Tween 85®, which is available from Uniqema; Alkamuls PSML-20®; Alkamuls PSMO-20®; Alkamuls PSTO-20®; Cremophor PS150®; Cremophor PS20®; Cremophor PS28®; Cremophor PS60®; Cremophor PS80®; Crill 3®; Crill 4®; Crill 6®; Crillet 3®; Crillet 4®; Crillet 6®; Glycomul L®; Glycomul O®; Glycomul S®; Glycomul TO®; Glycomul TS®; Hetsorb L-20®; Hetsorb L-4®; Hetsorb L-80-72%®; Hetsorb O-20®; Hetsorb O-5®; Hetsorb TO-20®; Lumisorb PSML-20 K®; Lumisorb PSML-20 NF®; Lumisorb PSMO-20 K®; Lumisorb PSMO-5 K®; Lumisorb PSMS-20 K®; Lumisorb PSTS-20 K®; Lumisorb PSTT-20 K®; Sorbax PML-20®; Sorbax PMO-20®; Sorbax PMO-5®; Sorbax PMP-20®; Sorbax PMS-20®; Sorbax PTO-20®; Sorbax PTS-20®; Sorbax SML®; Sorbax SMO®; Sorbax SMP®; Sorbax SMS®; Sorbax STO®; Sorbax STS®; Span 20®; Span 40®; Span 60®; Span 60K®; Span 65®; Span 80®; Span 85®; T-Maz 20®; T-Maz 28®; T-Maz 60K®; T-Maz 65K®; T-Maz 80®; T-Maz 80K®; T-Maz 81®; T-Maz 85®; and T-Maz 90®.

Sucrose and Glucose Esters and Derivatives, including but not limited to,

DeSulf GOS—P-60WCG®, which is available from DeForest Enterprises, Inc.; Glucam E-20 Distearate®, which is available from Amerchol Corp.; Glucamate DOE-120®, which is available from Amerchol Corp.; Glucamate SSE-20®, which is available from Amerchol Corp.; Glucate DO®, which is available from Amerchol Corp.; Glucate SS®, which is available from Amerchol Corp.; Glucopon 425 UP®, which is available from Cognis Corporation; Isolan IS®, which is available from Goldschmidt Chemical Corp.; Mazon 40®, which is available from BASF Corp.; Montanov 82®, which is available from Seppic Inc.; Montanov 202®, which is available from Seppic Inc.; Montanov S®, which is available from Seppic Inc.; Rheozan®, which is available from Rhodia, Inc.; Simulsol AS 48®, which is available from Seppic Inc.; Simulsol SL 4®, which is available from Seppic Inc.; Simulsol SL 10®, which is available from Seppic Inc.; Simulsol SL 11W®, which is available from Seppic Inc.; Simulsol SL 55®, which is available from Seppic Inc.; Suga Nate 100 and 160®, which is available from Colonial Chemical Co.; Tego Care 450®, which is available from Goldschmidt Chemical Corp.; Tego Care CG 90®, which is available from Goldschmidt Chemical Corp.; Tego Care PS®, which is available from Goldschmidt Chemical Corp.; Tegosoft PSE 141 G®, which is available from Goldschmidt Chemical Corp.; Tegotens G 826®, which is available from Goldschmidt Chemical Corp.; Triton BG-10 (70%)®, which is available from Dow Chemical Company; Triton CG-110 (60%)®, which is available from Dow Chemical Company; Wickenol 545®, which is available from Alzo International, Inc; Tego Care 150®; Tego Care 215®; and Triton CG-110 (60%)®.

Useful surfactants for the present invention also include: a sorbitan ester; Pluronic from BASF; Polysorbate 20; Polysorbate 40; Polysorbate 60; Polysorbate 80; a stearate; glyceryl stearate; isopropyl stearate; polyoxyl stearate; propylene glycol stearate; sucrose stearate; polyethylene glycol; polyethylene oxide; polypropylene oxide; a polyethylene oxide-polypropylene oxide copolymer; an alcohol ethoxylate; an alkylphenol ethoxylate; an alkyl glycoside; alkyl polyglycoside; a fatty alcohol; hydroxypropylmethyl cellulose; carboxymethyl cellulose; a polyacrylic acid; a Carbomer; a phospholipid; phosphatidyl choline; and phosphatidyl serine.

The compositions, in particular emulsions, of the present invention may optionally contain an active such as bimatoprost and may be comprised, but not limited to, the following combinations: Anise oil, and a sorbitan ester; Castor oil, and a sorbitan ester; Clove oil, and a sorbitan ester; Cassia oil, and a sorbitan ester; Cinnamon oil, and a sorbitan ester; an oil having a specific gravity from 0.90 to 0.95, and a sorbitan ester; Almond oil, and a sorbitan ester; Corn oil, and a sorbitan ester; Arachis oil, and a sorbitan ester; Cottonseed oil, and a sorbitan ester; Safflower oil, and a sorbitan ester; Maize oil, and a sorbitan ester; Linseed oil, and a sorbitan ester; Rapeseed oil, and a sorbitan ester; Soybean oil, and a sorbitan ester; Olive oil, and a sorbitan ester; Caraway oil, and a sorbitan ester; Rosemary oil, and a sorbitan ester; Peanut oil, and a sorbitan ester; Peppermint oil, and a sorbitan ester; Sunflower oil, and a sorbitan ester; Eucalyptus oil, and a sorbitan ester; Sesame oil, and a sorbitan ester; an oil having a specific gravity below 0.9, and a sorbitan ester; Mineral oil, and a sorbitan ester; Coriander oil, and a sorbitan ester; Lavender oil, and a sorbitan ester; Citronella oil, and a sorbitan ester; Juniper oil, and a sorbitan ester; Lemon oil, and a sorbitan ester; Orange oil, and a sorbitan ester; Clary sage oil, and a sorbitan ester; Nutmeg oil, and a sorbitan ester; Tea tree oil, and a sorbitan ester; an oil having a specific gravity from 0.95 to 1.07, and Polysorbate 80; Anise oil, and Polysorbate 80; Clove oil, and Polysorbate 80; Cassia oil, and Polysorbate 80; Cinnamon oil, and Polysorbate 80; an oil having a specific gravity from 0.90 to 0.95, and Polysorbate 80; Almond oil, and Polysorbate 80; Corn oil, and Polysorbate 80; Arachis oil, and Polysorbate 80; Cottonseed oil, and Polysorbate 80; Safflower oil, and Polysorbate 80; Maize oil, and Polysorbate 80; Linseed oil, and Polysorbate 80; Rapeseed oil, and Polysorbate 80; Soybean oil, and Polysorbate 80; Olive oil, and Polysorbate 80; Caraway oil, and Polysorbate 80; Rosemary oil, and Polysorbate 80; Peanut oil, and Polysorbate 80; Peppermint oil, and Polysorbate 80; Sunflower oil, and Polysorbate 80; Eucalyptus oil, and Polysorbate 80; Sesame oil, and Polysorbate 80; an oil having a specific gravity below 0.9, and Polysorbate 80; Mineral oil, and Polysorbate 80; Coriander oil, and Polysorbate 80; Lavender oil, and Polysorbate 80; Citronella oil, and Polysorbate 80; Juniper oil, and Polysorbate 80; Lemon oil, and Polysorbate 80; Orange oil, and Polysorbate 80; Clary sage oil, and Polysorbate 80; Nutmeg oil, and Polysorbate 80; Tea tree oil, and Polysorbate 80; an oil having a specific gravity from 0.95 to 1.07, and Polysorbate 60; Anise oil, and Polysorbate 60; Castor oil, and Polysorbate 60; Clove oil, and Polysorbate 60; Cassia oil, and Polysorbate 60; Cinnamon oil, and Polysorbate 60; an oil having a specific gravity from 0.90 to 0.95, and Polysorbate 60; Almond oil, and Polysorbate 60; Corn oil, and Polysorbate 60; Arachis oil, and Polysorbate 60; Cottonseed oil, and Polysorbate 60; Safflower oil, and Polysorbate 60; Maize oil, and Polysorbate 60; Linseed oil, and Polysorbate 60; Rapeseed oil, and Polysorbate 60; Soybean oil, and Polysorbate 60; Olive oil, and Polysorbate 60; Caraway oil, and Polysorbate 60; Rosemary oil, and Polysorbate 60; Peanut oil, and Polysorbate 60; Peppermint oil, and Polysorbate 60; Sunflower oil, and Polysorbate 60; Eucalyptus oil, and Polysorbate 60; Sesame oil, and Polysorbate 60; an oil having a specific gravity below 0.9, and Polysorbate 60; Mineral oil, and Polysorbate 60; Coriander oil, and Polysorbate 60; Lavender oil, and Polysorbate 60; Citronella oil, and Polysorbate 60; Juniper oil, and Polysorbate 60; Lemon oil, and Polysorbate 60; Orange oil, and Polysorbate 60; Clary sage oil, and Polysorbate 60; Nutmeg oil, and Polysorbate 60; Tea tree oil, and Polysorbate 60; an oil having a specific gravity from 0.95 to 1.07, and Polysorbate 40; Anise oil, and Polysorbate 40; Castor oil, and Polysorbate 40; Clove oil, and Polysorbate 40; Cassia oil, and Polysorbate 40; Cinnamon oil, and Polysorbate 40; an oil having a specific gravity from 0.90 to 0.95, and Polysorbate 40;

Almond oil, and Polysorbate 40;
    Corn oil, and Polysorbate 40;
    Arachis oil, and Polysorbate 40;
    Cottonseed oil, and Polysorbate 40;
    Safflower oil, and Polysorbate 40;
    Maize oil, and Polysorbate 40;
    Linseed oil, and Polysorbate 40;
    Rapeseed oil, and Polysorbate 40;
    Soybean oil, and Polysorbate 40;
    Olive oil, and Polysorbate 40;
    Caraway oil, and Polysorbate 40;
    Rosemary oil, and Polysorbate 40;
    Peanut oil, and Polysorbate 40;
    Peppermint oil, and Polysorbate 40;
    Sunflower oil, and Polysorbate 40;
    Eucalyptus oil, and Polysorbate 40;
    Sesame oil, and Polysorbate 40;
    an oil having a specific gravity below 0.9, and Polysorbate 40;
    Mineral oil, and Polysorbate 40;
    Coriander oil, and Polysorbate 40;
    Lavender oil, and Polysorbate 40;
    Citronella oil, and Polysorbate 40;
    Juniper oil, and Polysorbate 40;
    Lemon oil, and Polysorbate 40;
    Orange oil, and Polysorbate 40;
    Clary sage oil, and Polysorbate 40;
    Nutmeg oil, and Polysorbate 40;
    Tea tree oil, and Polysorbate 40;
    an oil having a specific gravity from 0.95 to 1.07, and Polysorbate 20;
    Anise oil, and Polysorbate 20;
    Castor oil, and Polysorbate 20;
    Clove oil, and Polysorbate 20;
    Cassia oil, and Polysorbate 20;
    Cinnamon oil, and Polysorbate 20;
    an oil having a specific gravity from 0.90 to 0.95, and Polysorbate 20;
    Almond oil, and Polysorbate 20;
    Corn oil, and Polysorbate 20;
    Arachis oil, and Polysorbate 20;
    Cottonseed oil, and Polysorbate 20;
    Safflower oil, and Polysorbate 20;
    Maize oil, and Polysorbate 20;
    Linseed oil, and Polysorbate 20;
    Rapeseed oil, and Polysorbate 20;
    Soybean oil, and Polysorbate 20;
    Olive oil, and Polysorbate 20;
    Caraway oil, and Polysorbate 20;
    Rosemary oil, and Polysorbate 20;
    Peanut oil, and Polysorbate 20;
    Peppermint oil, and Polysorbate 20;
    Sunflower oil, and Polysorbate 20;
    Eucalyptus oil, and Polysorbate 20;
    Sesame oil, and Polysorbate 20;
    an oil having a specific gravity below 0.9, and Polysorbate 20;
    Mineral oil, and Polysorbate 20;
    Coriander oil, and Polysorbate 20;
    Lavender oil, and Polysorbate 20;
    Citronella oil, and Polysorbate 20;
    Juniper oil, and Polysorbate 20;
    Lemon oil, and Polysorbate 20;
    Orange oil, and Polysorbate 20;
    Clary sage oil, and Polysorbate 20;
    Nutmeg oil, and Polysorbate 20;
    Tea tree oil, and Polysorbate 20;
    an oil having a specific gravity from 0.95 to 1.07, and a stearate surfactant;
    Anise oil, and a stearate surfactant;
    Castor oil, and a stearate surfactant;
    Clove oil, and a stearate surfactant;
    Cassia oil, and a stearate surfactant;
    Cinnamon oil, and a stearate surfactant;
    an oil having a specific gravity from 0.90 to 0.95, and a stearate surfactant;
    Almond oil, and a stearate surfactant;
    Corn oil, and a stearate surfactant;
    Arachis oil, and a stearate surfactant;
    Cottonseed oil, and a stearate surfactant;
    Safflower oil, and a stearate surfactant;
    Maize oil, and a stearate surfactant;
    Linseed oil, and a stearate surfactant;
    Rapeseed oil, and a stearate surfactant;
    Soybean oil, and a stearate surfactant;
    Olive oil, and a stearate surfactant;
    Caraway oil, and a stearate surfactant;
    Rosemary oil, and a stearate surfactant;
    Peanut oil, and a stearate surfactant;
    Peppermint oil, and a stearate surfactant;
    Sunflower oil, and a stearate surfactant;
    Eucalyptus oil, and a stearate surfactant;
    Sesame oil, and a stearate surfactant;
    an oil having a specific gravity below 0.9, and a stearate surfactant;
    Mineral oil, and a stearate surfactant;
    Coriander oil, and a stearate surfactant;
    Lavender oil, and a stearate surfactant;
    Citronella oil, and a stearate surfactant;
    Juniper oil, and a stearate surfactant;
    Lemon oil, and a stearate surfactant;
    Orange oil, and a stearate surfactant;
    Clary sage oil, and a stearate surfactant;
    Nutmeg oil, and a stearate surfactant;
    Tea tree oil, and a stearate surfactant;
    an oil having a specific gravity from 0.95 to 1.07, and glyceryl stearate;
    Anise oil, and glyceryl stearate;
    Castor oil, and glyceryl stearate;
    Clove oil, and glyceryl stearate;
    Cassia oil, and glyceryl stearate;
    Cinnamon oil, and glyceryl stearate;
    an oil having a specific gravity from 0.90 to 0.95, and glyceryl stearate;
    Almond oil, and glyceryl stearate;
    Corn oil, and glyceryl stearate;
    Arachis oil, and glyceryl stearate;
    Cottonseed oil, and glyceryl stearate;
    Safflower oil, and glyceryl stearate;
    Maize oil, and glyceryl stearate;
    Linseed oil, and glyceryl stearate;
    Rapeseed oil, and glyceryl stearate;
    Soybean oil, and glyceryl stearate;
    Olive oil, and glyceryl stearate;
    Caraway oil, and glyceryl stearate;

Rosemary oil, and glyceryl stearate;
Peanut oil, and glyceryl stearate;
Peppermint oil, and glyceryl stearate;
Sunflower oil, and glyceryl stearate;
Eucalyptus oil, and glyceryl stearate;
Sesame oil, and glyceryl stearate;
an oil having a specific gravity below 0.9, and glyceryl stearate;
Mineral oil, and glyceryl stearate;
Coriander oil, and glyceryl stearate;
Lavender oil, and glyceryl stearate;
Citronella oil, and glyceryl stearate;
Juniper oil, and glyceryl stearate;
Lemon oil, and glyceryl stearate;
Orange oil, and glyceryl stearate;
Clary sage oil, and glyceryl stearate;
Nutmeg oil, and glyceryl stearate;
Tea tree oil, and glyceryl stearate;
an oil having a specific gravity from 0.95 to 1.07, and isopropyl stearate;
Anise oil, and isopropyl stearate;
Castor oil, and isopropyl stearate;
Clove oil, and isopropyl stearate;
Cassia oil, and isopropyl stearate;
Cinnamon oil, and isopropyl stearate;
an oil having a specific gravity from 0.90 to 0.95, and isopropyl stearate;
Almond oil, and isopropyl stearate;
Corn oil, and isopropyl stearate;
Arachis oil, and isopropyl stearate;
Cottonseed oil, and isopropyl stearate;
Safflower oil, and isopropyl stearate;
Maize oil, and isopropyl stearate;
Linseed oil, and isopropyl stearate;
Rapeseed oil, and isopropyl stearate;
Soybean oil, and isopropyl stearate;
Olive oil, and isopropyl stearate;
Caraway oil, and isopropyl stearate;
Rosemary oil, and isopropyl stearate;
Peanut oil, and isopropyl stearate;
Peppermint oil, and isopropyl stearate;
Sunflower oil, and isopropyl stearate;
Eucalyptus oil, and isopropyl stearate;
Sesame oil, and isopropyl stearate;
an oil having a specific gravity below 0.9, and isopropyl stearate;
Mineral oil, and isopropyl stearate;
Coriander oil, and isopropyl stearate;
Lavender oil, and isopropyl stearate;
Citronella oil, and isopropyl stearate;
Juniper oil, and isopropyl stearate;
Lemon oil, and isopropyl stearate;
Orange oil, and isopropyl stearate;
Clary sage oil, and isopropyl stearate;
Nutmeg oil, and isopropyl stearate;
Tea tree oil, and isopropyl stearate;
an oil having a specific gravity from 0.95 to 1.07, and polyoxyl stearate;
Anise oil, and polyoxyl stearate;
Castor oil, and polyoxyl stearate;
Clove oil, and polyoxyl stearate;
Cassia oil, and polyoxyl stearate;
Cinnamon oil, and polyoxyl stearate;
an oil having a specific gravity from 0.90 to 0.95, and polyoxyl stearate;
Almond oil, and polyoxyl stearate;
Corn oil, and polyoxyl stearate;
Arachis oil, and polyoxyl stearate;
Cottonseed oil, and polyoxyl stearate;
Safflower oil, and polyoxyl stearate;
Maize oil, and polyoxyl stearate;
Linseed oil, and polyoxyl stearate;
Rapeseed oil, and polyoxyl stearate;
Soybean oil, and polyoxyl stearate;
Olive oil, and polyoxyl stearate;
Caraway oil, and polyoxyl stearate;
Rosemary oil, and polyoxyl stearate;
Peanut oil, and polyoxyl stearate;
Peppermint oil, and polyoxyl stearate;
Sunflower oil, and polyoxyl stearate;
Eucalyptus oil, and polyoxyl stearate;
Sesame oil, and polyoxyl stearate;
an oil having a specific gravity below 0.9, and polyoxyl stearate;
Mineral oil, and polyoxyl stearate;
Coriander oil, and polyoxyl stearate;
Lavender oil, and polyoxyl stearate;
Citronella oil, and polyoxyl stearate;
Juniper oil, and polyoxyl stearate;
Lemon oil, and polyoxyl stearate;
Orange oil, and polyoxyl stearate;
Clary sage oil, and polyoxyl stearate;
Nutmeg oil, and polyoxyl stearate;
Tea tree oil, and polyoxyl stearate;
an oil having a specific gravity from 0.95 to 1.07, and propylene glycol stearate;
Anise oil, and propylene glycol stearate;
Castor oil, and propylene glycol stearate;
Clove oil, and propylene glycol stearate;
Cassia oil, and propylene glycol stearate;
Cinnamon oil, and propylene glycol stearate;
an oil having a specific gravity from 0.90 to 0.95, and propylene glycol stearate;
Almond oil, and propylene glycol stearate;
Corn oil, and propylene glycol stearate;
Arachis oil, and propylene glycol stearate;
Cottonseed oil, and propylene glycol stearate;
Safflower oil, and propylene glycol stearate;
Maize oil, and propylene glycol stearate;
Linseed oil, and propylene glycol stearate;
Rapeseed oil, and propylene glycol stearate;
Soybean oil, and propylene glycol stearate;
Olive oil, and propylene glycol stearate;
Caraway oil, and propylene glycol stearate;
Rosemary oil, and propylene glycol stearate;
Peanut oil, and propylene glycol stearate;
Peppermint oil, and propylene glycol stearate;
Sunflower oil, and propylene glycol stearate;
Eucalyptus oil, and propylene glycol stearate;
Sesame oil, and propylene glycol stearate;
an oil having a specific gravity below 0.9, and propylene glycol stearate;
Mineral oil, and propylene glycol stearate;
Coriander oil, and propylene glycol stearate;
Lavender oil, and propylene glycol stearate;
Citronella oil, and propylene glycol stearate;
Juniper oil, and propylene glycol stearate;
Lemon oil, and propylene glycol stearate;
Orange oil, and propylene glycol stearate;
Clary sage oil, and propylene glycol stearate;
Nutmeg oil, and propylene glycol stearate;
Tea tree oil, and propylene glycol stearate;
an oil having a specific gravity from 0.95 to 1.07, and sucrose stearate;

Anise oil, and sucrose stearate;
Castor oil, and sucrose stearate;
Clove oil, and sucrose stearate;
Cassia oil, and sucrose stearate;
Cinnamon oil, and sucrose stearate;
an oil having a specific gravity from 0.90 to 0.95, and sucrose stearate;
Almond oil, and sucrose stearate;
Corn oil, and sucrose stearate;
Arachis oil, and sucrose stearate;
Cottonseed oil, and sucrose stearate;
Safflower oil, and sucrose stearate;
Maize oil, and sucrose stearate;
Linseed oil, and sucrose stearate;
Rapeseed oil, and sucrose stearate;
Soybean oil, and sucrose stearate;
Olive oil, and sucrose stearate;
Caraway oil, and sucrose stearate;
Rosemary oil, and sucrose stearate;
Peanut oil, and sucrose stearate;
Peppermint oil, and sucrose stearate;
Sunflower oil, and sucrose stearate;
Eucalyptus oil, and sucrose stearate;
Sesame oil, and sucrose stearate;
an oil having a specific gravity below 0.9, and sucrose stearate;
Mineral oil, and sucrose stearate;
Coriander oil, and sucrose stearate;
Lavender oil, and sucrose stearate;
Citronella oil, and sucrose stearate;
Juniper oil, and sucrose stearate;
Lemon oil, and sucrose stearate;
Orange oil, and sucrose stearate;
Clary sage oil, and sucrose stearate;
Nutmeg oil, and sucrose stearate;
Tea tree oil, and sucrose stearate;
an oil having a specific gravity from 0.95 to 1.07, and polyethylene glycol;
Anise oil, and polyethylene glycol;
Castor oil, and polyethylene glycol;
Clove oil, and polyethylene glycol;
Cassia oil, and polyethylene glycol;
Cinnamon oil, and polyethylene glycol;
an oil having a specific gravity from 0.90 to 0.95, and polyethylene glycol;
Almond oil, and polyethylene glycol;
Corn oil, and polyethylene glycol;
Arachis oil, and polyethylene glycol;
Cottonseed oil, and polyethylene glycol;
Safflower oil, and polyethylene glycol;
Maize oil, and polyethylene glycol;
Linseed oil, and polyethylene glycol;
Rapeseed oil, and polyethylene glycol;
Soybean oil, and polyethylene glycol;
Olive oil, and polyethylene glycol;
Caraway oil, and polyethylene glycol;
Rosemary oil, and polyethylene glycol;
Peanut oil, and polyethylene glycol;
Peppermint oil, and polyethylene glycol;
Sunflower oil, and polyethylene glycol;
Eucalyptus oil, and polyethylene glycol;
Sesame oil, and polyethylene glycol;
an oil having a specific gravity below 0.9, and polyethylene glycol;
Mineral oil, and polyethylene glycol;
Coriander oil, and polyethylene glycol;
Lavender oil, and polyethylene glycol;
Citronella oil, and polyethylene glycol;
Juniper oil, and polyethylene glycol;
Lemon oil, and polyethylene glycol;
Orange oil, and polyethylene glycol;
Clary sage oil, and polyethylene glycol;
Nutmeg oil, and polyethylene glycol;
Tea tree oil, and polyethylene glycol;
an oil having a specific gravity from 0.95 to 1.07, and polyethylene oxide;
Anise oil, and polyethylene oxide;
Castor oil, and polyethylene oxide;
Clove oil, and polyethylene oxide;
Cassia oil, and polyethylene oxide;
Cinnamon oil, and polyethylene oxide;
an oil having a specific gravity from 0.90 to 0.95, and polyethylene oxide;
Almond oil, and polyethylene oxide;
Corn oil, and polyethylene oxide;
Arachis oil, and polyethylene oxide;
Cottonseed oil, and polyethylene oxide;
Safflower oil, and polyethylene oxide;
Maize oil, and polyethylene oxide;
Linseed oil, and polyethylene oxide;
Rapeseed oil, and polyethylene oxide;
Soybean oil, and polyethylene oxide;
Olive oil, and polyethylene oxide;
Caraway oil, and polyethylene oxide;
Rosemary oil, and polyethylene oxide;
Peanut oil, and polyethylene oxide;
Peppermint oil, and polyethylene oxide;
Sunflower oil, and polyethylene oxide;
Eucalyptus oil, and polyethylene oxide;
Sesame oil, and polyethylene oxide;
an oil having a specific gravity below 0.9, and polyethylene oxide;
Mineral oil, and polyethylene oxide;
Coriander oil, and polyethylene oxide;
Lavender oil, and polyethylene oxide;
Citronella oil, and polyethylene oxide;
Juniper oil, and polyethylene oxide;
Lemon oil, and polyethylene oxide;
Orange oil, and polyethylene oxide;
Clary sage oil, and polyethylene oxide;
Nutmeg oil, and polyethylene oxide;
Tea tree oil, and polyethylene oxide;
an oil having a specific gravity from 0.95 to 1.07, and polypropylene oxide;
Anise oil, and polypropylene oxide;
Castor oil, and polypropylene oxide;
Clove oil, and polypropylene oxide;
Cassia oil, and polypropylene oxide;
Cinnamon oil, and polypropylene oxide;
an oil having a specific gravity from 0.90 to 0.95, and polypropylene oxide;
Almond oil, and polypropylene oxide;
Corn oil, and polypropylene oxide;
Arachis oil, and polypropylene oxide;
Cottonseed oil, and polypropylene oxide;
Safflower oil, and polypropylene oxide;
Maize oil, and polypropylene oxide;
Linseed oil, and polypropylene oxide;
Rapeseed oil, and polypropylene oxide;
Soybean oil, and polypropylene oxide;
Olive oil, and polypropylene oxide;
Caraway oil, and polypropylene oxide;
Rosemary oil, and polypropylene oxide;
Peanut oil, and polypropylene oxide;

Peppermint oil, and polypropylene oxide;
Sunflower oil, and polypropylene oxide;
Eucalyptus oil, and polypropylene oxide;
Sesame oil, and polypropylene oxide;
an oil having a specific gravity below 0.9, and polypropylene oxide;
Mineral oil, and polypropylene oxide;
Coriander oil, and polypropylene oxide;
Lavender oil, and polypropylene oxide;
Citronella oil, and polypropylene oxide;
Juniper oil, and polypropylene oxide;
Lemon oil, and polypropylene oxide;
Orange oil, and polypropylene oxide;
Clary sage oil, and polypropylene oxide;
Nutmeg oil, and polypropylene oxide;
Tea tree oil, and polypropylene oxide;
an oil having a specific gravity from 0.95 to 1.07, and a polyethylene oxide-polypropylene oxide copolymer;
Anise oil, and a polyethylene oxide-polypropylene oxide copolymer;
Castor oil, and a polyethylene oxide-polypropylene oxide copolymer;
Clove oil, and a polyethylene oxide-polypropylene oxide copolymer;
Cassia oil, and a polyethylene oxide-polypropylene oxide copolymer;
Cinnamon oil, and a polyethylene oxide-polypropylene oxide copolymer;
an oil having a specific gravity from 0.90 to 0.95, and a polyethylene oxide-polypropylene oxide copolymer;
Almond oil, and a polyethylene oxide-polypropylene oxide copolymer;
Corn oil, and a polyethylene oxide-polypropylene oxide copolymer;
Arachis oil, and a polyethylene oxide-polypropylene oxide copolymer;
Cottonseed oil, and a polyethylene oxide-polypropylene oxide copolymer;
Safflower oil, and a polyethylene oxide-polypropylene oxide copolymer;
Maize oil, and a polyethylene oxide-polypropylene oxide copolymer;
Linseed oil, and a polyethylene oxide-polypropylene oxide copolymer;
Rapeseed oil, and a polyethylene oxide-polypropylene oxide copolymer;
Soybean oil, and a polyethylene oxide-polypropylene oxide copolymer;
Olive oil, and a polyethylene oxide-polypropylene oxide copolymer;
Caraway oil, and a polyethylene oxide-polypropylene oxide copolymer;
Rosemary oil, and a polyethylene oxide-polypropylene oxide copolymer;
Peanut oil, and a polyethylene oxide-polypropylene oxide copolymer;
Peppermint oil, and a polyethylene oxide-polypropylene oxide copolymer;
Sunflower oil, and a polyethylene oxide-polypropylene oxide copolymer;
Eucalyptus oil, and a polyethylene oxide-polypropylene oxide copolymer;
Sesame oil, and a polyethylene oxide-polypropylene oxide copolymer;
an oil having a specific gravity below 0.9, and a polyethylene oxide-polypropylene oxide copolymer;
Mineral oil, and a polyethylene oxide-polypropylene oxide copolymer;
Coriander oil, and a polyethylene oxide-polypropylene oxide copolymer;
Lavender oil, and a polyethylene oxide-polypropylene oxide copolymer;
Citronella oil, and a polyethylene oxide-polypropylene oxide copolymer;
Juniper oil, and a polyethylene oxide-polypropylene oxide copolymer;
Lemon oil, and a polyethylene oxide-polypropylene oxide copolymer;
Orange oil, and a polyethylene oxide-polypropylene oxide copolymer;
Clary sage oil, and a polyethylene oxide-polypropylene oxide copolymer;
Nutmeg oil, and a polyethylene oxide-polypropylene oxide copolymer;
Tea tree oil, and a polyethylene oxide-polypropylene oxide copolymer;
an oil having a specific gravity from 0.95 to 1.07, and an alcohol ethoxylate;
Anise oil, and an alcohol ethoxylate;
Castor oil, and an alcohol ethoxylate;
Clove oil, and an alcohol ethoxylate;
Cassia oil, and an alcohol ethoxylate;
Cinnamon oil, and an alcohol ethoxylate; an oil having a specific gravity from 0.90 to 0.95, and an alcohol ethoxylate;
Almond oil, and an alcohol ethoxylate;
Corn oil, and an alcohol ethoxylate;
Arachis oil, and an alcohol ethoxylate;
Cottonseed oil, and an alcohol ethoxylate;
Safflower oil, and an alcohol ethoxylate;
Maize oil, and an alcohol ethoxylate;
Linseed oil, and an alcohol ethoxylate;
Rapeseed oil, and an alcohol ethoxylate;
Soybean oil, and an alcohol ethoxylate;
Olive oil, and an alcohol ethoxylate;
Caraway oil, and an alcohol ethoxylate;
Rosemary oil, and an alcohol ethoxylate;
Peanut oil, and an alcohol ethoxylate;
Peppermint oil, and an alcohol ethoxylate;
Sunflower oil, and an alcohol ethoxylate;
Eucalyptus oil, and an alcohol ethoxylate;
Sesame oil, and an alcohol ethoxylate;
an oil having a specific gravity below 0.9, and an alcohol ethoxylate;
Mineral oil, and an alcohol ethoxylate;
Coriander oil, and an alcohol ethoxylate;
Lavender oil, and an alcohol ethoxylate;
Citronella oil, and an alcohol ethoxylate;
Juniper oil, and an alcohol ethoxylate;
Lemon oil, and an alcohol ethoxylate;
Orange oil, and an alcohol ethoxylate;
Clary sage oil, and an alcohol ethoxylate;
Nutmeg oil, and an alcohol ethoxylate;
Tea tree oil, and an alcohol ethoxylate;
an oil having a specific gravity from 0.95 to 1.07, and an alkylphenol ethoxylate;
Anise oil, and an alkylphenol ethoxylate;
Castor oil, and an alkylphenol ethoxylate;
Clove oil, and an alkylphenol ethoxylate;
Cassia oil, and an alkylphenol ethoxylate;
Cinnamon oil, and an alkylphenol ethoxylate;
an oil having a specific gravity from 0.90 to 0.95, and an alkylphenol ethoxylate;
Almond oil, and an alkylphenol ethoxylate;

Corn oil, and an alkylphenol ethoxylate;
Arachis oil, and an alkylphenol ethoxylate;
Cottonseed oil, and an alkylphenol ethoxylate;
Safflower oil, and an alkylphenol ethoxylate;
Maize oil, and an alkylphenol ethoxylate;
Linseed oil, and an alkylphenol ethoxylate;
Rapeseed oil, and an alkylphenol ethoxylate;
Soybean oil, and an alkylphenol ethoxylate;
Olive oil, and an alkylphenol ethoxylate;
Caraway oil, and an alkylphenol ethoxylate;
Rosemary oil, and an alkylphenol ethoxylate;
Peanut oil, and an alkylphenol ethoxylate;
Peppermint oil, and an alkylphenol ethoxylate;
Sunflower oil, and an alkylphenol ethoxylate;
Eucalyptus oil, and an alkylphenol ethoxylate;
Sesame oil, and an alkylphenol ethoxylate;
an oil having a specific gravity below 0.9, and an alkylphenol ethoxylate;
Mineral oil, and an alkylphenol ethoxylate;
Coriander oil, and an alkylphenol ethoxylate;
Lavender oil, and an alkylphenol ethoxylate;
Citronella oil, and an alkylphenol ethoxylate;
Juniper oil, and an alkylphenol ethoxylate;
Lemon oil, and an alkylphenol ethoxylate;
Orange oil, and an alkylphenol ethoxylate;
Clary sage oil, and an alkylphenol ethoxylate;
Nutmeg oil, and an alkylphenol ethoxylate;
Tea tree oil, and an alkylphenol ethoxylate;
an oil having a specific gravity from 0.95 to 1.07, and an alkyl glycoside;
Anise oil, and an alkyl glycoside;
Castor oil, and an alkyl glycoside;
Clove oil, and an alkyl glycoside;
Cassia oil, and an alkyl glycoside;
Cinnamon oil, and an alkyl glycoside;
an oil having a specific gravity from 0.90 to 0.95, and an alkyl glycoside;
Almond oil, and an alkyl glycoside;
Corn oil, and an alkyl glycoside;
Arachis oil, and an alkyl glycoside;
Cottonseed oil, and an alkyl glycoside;
Safflower oil, and an alkyl glycoside;
Maize oil, and an alkyl glycoside;
Linseed oil, and an alkyl glycoside;
Rapeseed oil, and an alkyl glycoside;
Soybean oil, and an alkyl glycoside;
Olive oil, and an alkyl glycoside;
Caraway oil, and an alkyl glycoside;
Rosemary oil, and an alkyl glycoside;
Peanut oil, and an alkyl glycoside;
Peppermint oil, and an alkyl glycoside;
Sunflower oil, and an alkyl glycoside;
Eucalyptus oil, and an alkyl glycoside;
Sesame oil, and an alkyl glycoside;
an oil having a specific gravity below 0.9, and an alkyl glycoside;
Mineral oil, and an alkyl glycoside;
Coriander oil, and an alkyl glycoside;
Lavender oil, and an alkyl glycoside;
Citronella oil, and an alkyl glycoside;
Juniper oil, and an alkyl glycoside;
Lemon oil, and an alkyl glycoside;
Orange oil, and an alkyl glycoside;
Clary sage oil, and an alkyl glycoside;
Nutmeg oil, and an alkyl glycoside;
Tea tree oil, and an alkyl glycoside;
an oil having a specific gravity from 0.95 to 1.07, and an alkyl polyglycoside;
Anise oil, and an alkyl polyglycoside;
Castor oil, and an alkyl polyglycoside;
Clove oil, and an alkyl polyglycoside;
Cassia oil, and an alkyl polyglycoside;
Cinnamon oil, and an alkyl polyglycoside;
an oil having a specific gravity from 0.90 to 0.95, and an alkyl polyglycoside;
Almond oil, and an alkyl polyglycoside;
Corn oil, and an alkyl polyglycoside;
Arachis oil, and an alkyl polyglycoside;
Cottonseed oil, and an alkyl polyglycoside;
Safflower oil, and an alkyl polyglycoside;
Maize oil, and an alkyl polyglycoside;
Linseed oil, and an alkyl polyglycoside;
Rapeseed oil, and an alkyl polyglycoside;
Soybean oil, and an alkyl polyglycoside;
Olive oil, and an alkyl polyglycoside;
Caraway oil, and an alkyl polyglycoside;
Rosemary oil, and an alkyl polyglycoside;
Peanut oil, and an alkyl polyglycoside;
Peppermint oil, and an alkyl polyglycoside;
Sunflower oil, and an alkyl polyglycoside;
Eucalyptus oil, and an alkyl polyglycoside;
Sesame oil, and an alkyl polyglycoside;
an oil having a specific gravity below 0.9, and an alkyl polyglycoside;
Mineral oil, and an alkyl polyglycoside;
Coriander oil, and an alkyl polyglycoside;
Lavender oil, and an alkyl polyglycoside;
Citronella oil, and an alkyl polyglycoside;
Juniper oil, and an alkyl polyglycoside;
Lemon oil, and an alkyl polyglycoside;
Orange oil, and an alkyl polyglycoside;
Clary sage oil, and an alkyl polyglycoside;
Nutmeg oil, and an alkyl polyglycoside;
Tea tree oil, and an alkyl polyglycoside;
an oil having a specific gravity from 0.95 to 1.07, and a fatty alcohol;
Anise oil, and a fatty alcohol;
Castor oil, and a fatty alcohol;
Clove oil, and a fatty alcohol;
Cassia oil, and a fatty alcohol;
Cinnamon oil, and a fatty alcohol;
an oil having a specific gravity from 0.90 to 0.95, and a fatty alcohol;
Almond oil, and a fatty alcohol;
Corn oil, and a fatty alcohol;
Arachis oil, and a fatty alcohol;
Cottonseed oil, and a fatty alcohol;
Safflower oil, and a fatty alcohol;
Maize oil, and a fatty alcohol;
Linseed oil, and a fatty alcohol;
Rapeseed oil, and a fatty alcohol;
Soybean oil, and a fatty alcohol;
Olive oil, and a fatty alcohol;
Caraway oil, and a fatty alcohol;
Rosemary oil, and a fatty alcohol;
Peanut oil, and a fatty alcohol;
Peppermint oil, and a fatty alcohol;
Sunflower oil, and a fatty alcohol;
Eucalyptus oil, and a fatty alcohol;
Sesame oil, and a fatty alcohol;
an oil having a specific gravity below 0.9, and a fatty alcohol;
Mineral oil, and a fatty alcohol;

Coriander oil, and a fatty alcohol;
Lavender oil, and a fatty alcohol;
Citronella oil, and a fatty alcohol;
Juniper oil, and a fatty alcohol;
Lemon oil, and a fatty alcohol;
Orange oil, and a fatty alcohol;
Clary sage oil, and a fatty alcohol;
Nutmeg oil, and a fatty alcohol;
Tea tree oil, and a fatty alcohol;
an oil having a specific gravity from 0.95 to 1.07, and a cellulose derivative;
Anise oil, and a cellulose derivative;
Castor oil, and a cellulose derivative;
Clove oil, and a cellulose derivative;
Cassia oil, and a cellulose derivative;
Cinnamon oil, and a cellulose derivative;
an oil having a specific gravity from 0.90 to 0.95, and a cellulose derivative;
Almond oil, and a cellulose derivative;
Corn oil, and a cellulose derivative;
Arachis oil, and a cellulose derivative;
Cottonseed oil, and a cellulose derivative;
Safflower oil, and a cellulose derivative;
Maize oil, and a cellulose derivative;
Linseed oil, and a cellulose derivative;
Rapeseed oil, and a cellulose derivative;
Soybean oil, and a cellulose derivative;
Olive oil, and a cellulose derivative;
Caraway oil, and a cellulose derivative;
Rosemary oil, and a cellulose derivative;
Peanut oil, and a cellulose derivative;
Peppermint oil, and a cellulose derivative;
Sunflower oil, and a cellulose derivative;
Eucalyptus oil, and a cellulose derivative;
Sesame oil, and a cellulose derivative;
an oil having a specific gravity below 0.9, and a cellulose derivative;
Mineral oil, and a cellulose derivative;
Coriander oil, and a cellulose derivative;
Lavender oil, and a cellulose derivative;
Citronella oil, and a cellulose derivative;
Juniper oil, and a cellulose derivative;
Lemon oil, and a cellulose derivative;
Orange oil, and a cellulose derivative;
Clary sage oil, and a cellulose derivative;
Nutmeg oil, and a cellulose derivative;
Tea tree oil, and a cellulose derivative;
an oil having a specific gravity from 0.95 to 1.07, and hydroxypropylmethyl cellulose;
Anise oil, and hydroxypropylmethyl cellulose;
Castor oil, and hydroxypropylmethyl cellulose;
Clove oil, and hydroxypropylmethyl cellulose;
Cassia oil, and hydroxypropylmethyl cellulose;
Cinnamon oil, and hydroxypropylmethyl cellulose;
an oil having a specific gravity from 0.90 to 0.95, and hydroxypropylmethyl cellulose;
Almond oil, and hydroxypropylmethyl cellulose;
Corn oil, and hydroxypropylmethyl cellulose;
Arachis oil, and hydroxypropylmethyl cellulose;
Cottonseed oil, and hydroxypropylmethyl cellulose;
Safflower oil, and hydroxypropylmethyl cellulose;
Maize oil, and hydroxypropylmethyl cellulose;
Linseed oil, and hydroxypropylmethyl cellulose;
Rapeseed oil, and hydroxypropylmethyl cellulose;
Soybean oil, and hydroxypropylmethyl cellulose;
Olive oil, and hydroxypropylmethyl cellulose;
Caraway oil, and hydroxypropylmethyl cellulose;
Rosemary oil, and hydroxypropylmethyl cellulose;
Peanut oil, and hydroxypropylmethyl cellulose;
Peppermint oil, and hydroxypropylmethyl cellulose;
Sunflower oil, and hydroxypropylmethyl cellulose;
Eucalyptus oil, and hydroxypropylmethyl cellulose;
Sesame oil, and hydroxypropylmethyl cellulose;
an oil having a specific gravity below 0.9, and hydroxypropylmethyl cellulose;
Mineral oil, and hydroxypropylmethyl cellulose;
Coriander oil, and hydroxypropylmethyl cellulose;
Lavender oil, and hydroxypropylmethyl cellulose;
Citronella oil, and hydroxypropylmethyl cellulose;
Juniper oil, and hydroxypropylmethyl cellulose;
Lemon oil, and hydroxypropylmethyl cellulose;
Orange oil, and hydroxypropylmethyl cellulose;
Clary sage oil, and hydroxypropylmethyl cellulose;
Nutmeg oil, and hydroxypropylmethyl cellulose;
Tea tree oil, and hydroxypropylmethyl cellulose;
an oil having a specific gravity from 0.95 to 1.07, and carboxymethyl cellulose;
Anise oil, and carboxymethyl cellulose;
Castor oil, and carboxymethyl cellulose;
Clove oil, and carboxymethyl cellulose;
Cassia oil, and carboxymethyl cellulose;
Cinnamon oil, and carboxymethyl cellulose;
an oil having a specific gravity from 0.90 to 0.95, and carboxymethyl cellulose;
Almond oil, and carboxymethyl cellulose;
Corn oil, and carboxymethyl cellulose;
Arachis oil, and carboxymethyl cellulose;
Cottonseed oil, and carboxymethyl cellulose;
Safflower oil, and carboxymethyl cellulose;
Maize oil, and carboxymethyl cellulose;
Linseed oil, and carboxymethyl cellulose;
Rapeseed oil, and carboxymethyl cellulose;
Soybean oil, and carboxymethyl cellulose;
Olive oil, and carboxymethyl cellulose;
Caraway oil, and carboxymethyl cellulose;
Rosemary oil, and carboxymethyl cellulose;
Peanut oil, and carboxymethyl cellulose;
Peppermint oil, and carboxymethyl cellulose;
Sunflower oil, and carboxymethyl cellulose;
Eucalyptus oil, and carboxymethyl cellulose;
Sesame oil, and carboxymethyl cellulose;
an oil having a specific gravity below 0.9, and carboxymethyl cellulose;
Mineral oil, and carboxymethyl cellulose;
Coriander oil, and carboxymethyl cellulose;
Lavender oil, and carboxymethyl cellulose;
Citronella oil, and carboxymethyl cellulose;
Juniper oil, and carboxymethyl cellulose;
Lemon oil, and carboxymethyl cellulose;
Orange oil, and carboxymethyl cellulose;
Clary sage oil, and carboxymethyl cellulose;
Nutmeg oil, and carboxymethyl cellulose;
Tea tree oil, and carboxymethyl cellulose;
an oil having a specific gravity from 0.95 to 1.07, and a polyacrylic acid;
Anise oil, and a polyacrylic acid;
Castor oil, and a polyacrylic acid;
Clove oil, and a polyacrylic acid;
Cassia oil, and a polyacrylic acid;
Cinnamon oil, and a polyacrylic acid;
an oil having a specific gravity from 0.90 to 0.95, and a polyacrylic acid;
Almond oil, and a polyacrylic acid;
Corn oil, and a polyacrylic acid;

Arachis oil, and a polyacrylic acid;
Cottonseed oil, and a polyacrylic acid;
Safflower oil, and a polyacrylic acid;
Maize oil, and a polyacrylic acid;
Linseed oil, and a polyacrylic acid;
Rapeseed oil, and a polyacrylic acid;
Soybean oil, and a polyacrylic acid;
Olive oil, and a polyacrylic acid;
Caraway oil, and a polyacrylic acid;
Rosemary oil, and a polyacrylic acid;
Peanut oil, and a polyacrylic acid;
Peppermint oil, and a polyacrylic acid;
Sunflower oil, and a polyacrylic acid;
Eucalyptus oil, and a polyacrylic acid;
Sesame oil, and a polyacrylic acid;
an oil having a specific gravity below 0.9, and a polyacrylic acid;
Mineral oil, and a polyacrylic acid;
Coriander oil, and a polyacrylic acid;
Lavender oil, and a polyacrylic acid;
Citronella oil, and a polyacrylic acid;
Juniper oil, and a polyacrylic acid;
Lemon oil, and a polyacrylic acid;
Orange oil, and a polyacrylic acid;
Clary sage oil, and a polyacrylic acid;
Nutmeg oil, and a polyacrylic acid;
Tea tree oil, and a polyacrylic acid;
an oil having a specific gravity from 0.95 to 1.07, and a Carbomer;
Anise oil, and a Carbomer;
Castor oil, and a Carbomer;
Clove oil, and a Carbomer;
Cassia oil, and a Carbomer;
Cinnamon oil, and a Carbomer;
an oil having a specific gravity from 0.90 to 0.95, and a Carbomer;
Almond oil, and a Carbomer;
Corn oil, and a Carbomer;
Arachis oil, and a Carbomer;
Cottonseed oil, and a Carbomer;
Safflower oil, and a Carbomer;
Maize oil, and a Carbomer;
Linseed oil, and a Carbomer;
Rapeseed oil, and a Carbomer;
Soybean oil, and a Carbomer;
Olive oil, and a Carbomer;
Caraway oil, and a Carbomer;
Rosemary oil, and a Carbomer;
Peanut oil, and a Carbomer;
Peppermint oil, and a Carbomer;
Sunflower oil, and a Carbomer;
Eucalyptus oil, and a Carbomer;
Sesame oil, and a Carbomer;
an oil having a specific gravity below 0.9, and a Carbomer;
Mineral oil, and a Carbomer;
Coriander oil, and a Carbomer;
Lavender oil, and a Carbomer;
Citronella oil, and a Carbomer;
Juniper oil, and a Carbomer;
Lemon oil, and a Carbomer;
Orange oil, and a Carbomer;
Clary sage oil, and a Carbomer;
Nutmeg oil, and a Carbomer;
Tea tree oil, and a Carbomer;
an oil having a specific gravity from 0.95 to 1.07, and a phospholipid;
Anise oil, and a phospholipid;
Castor oil, and a phospholipid;
Clove oil, and a phospholipid;
Cassia oil, and a phospholipid;
Cinnamon oil, and a phospholipid;
an oil having a specific gravity from 0.90 to 0.95, and a phospholipid;
Almond oil, and a phospholipid;
Corn oil, and a phospholipid;
Arachis oil, and a phospholipid;
Cottonseed oil, and a phospholipid;
Safflower oil, and a phospholipid;
Maize oil, and a phospholipid;
Linseed oil, and a phospholipid;
Rapeseed oil, and a phospholipid;
Soybean oil, and a phospholipid;
Olive oil, and a phospholipid;
Caraway oil, and a phospholipid;
Rosemary oil, and a phospholipid;
Peanut oil, and a phospholipid;
Peppermint oil, and a phospholipid;
Sunflower oil, and a phospholipid;
Eucalyptus oil, and a phospholipid;
Sesame oil, and a phospholipid;
an oil having a specific gravity below 0.9, and a phospholipid;
Mineral oil, and a phospholipid;
Coriander oil, and a phospholipid;
Lavender oil, and a phospholipid;
Citronella oil, and a phospholipid;
Juniper oil, and a phospholipid;
Lemon oil, and a phospholipid;
Orange oil, and a phospholipid;
Clary sage oil, and a phospholipid;
Nutmeg oil, and a phospholipid;
Tea tree oil, and a phospholipid;
an oil having a specific gravity from 0.95 to 1.07, and phosphatidyl choline;
Anise oil, and phosphatidyl choline;
Castor oil, and phosphatidyl choline;
Clove oil, and phosphatidyl choline;
Cassia oil, and phosphatidyl choline;
Cinnamon oil, and phosphatidyl choline;
an oil having a specific gravity from 0.90 to 0.95, and phosphatidyl choline;
Almond oil, and phosphatidyl choline;
Corn oil, and phosphatidyl choline;
Arachis oil, and phosphatidyl choline;
Cottonseed oil, and phosphatidyl choline;
Safflower oil, and phosphatidyl choline;
Maize oil, and phosphatidyl choline;
Linseed oil, and phosphatidyl choline;
Rapeseed oil, and phosphatidyl choline;
Soybean oil, and phosphatidyl choline;
Olive oil, and phosphatidyl choline;
Caraway oil, and phosphatidyl choline;
Rosemary oil, and phosphatidyl choline;
Peanut oil, and phosphatidyl choline;
Peppermint oil, and phosphatidyl choline;
Sunflower oil, and phosphatidyl choline;
Eucalyptus oil, and phosphatidyl choline;
Sesame oil, and phosphatidyl choline;
an oil having a specific gravity below 0.9, and phosphatidyl choline;
Mineral oil, and phosphatidyl choline;
Coriander oil, and phosphatidyl choline;
Lavender oil, and phosphatidyl choline;
Citronella oil, and phosphatidyl choline;

Juniper oil, and phosphatidyl choline;
Lemon oil, and phosphatidyl choline;
Orange oil, and phosphatidyl choline;
Clary sage oil, and phosphatidyl choline;
Nutmeg oil, and phosphatidyl choline;
Tea tree oil, and phosphatidyl choline;
an oil having a specific gravity from 0.95 to 1.07, and phosphatidyl serine;
Anise oil, and phosphatidyl serine;
Castor oil, and phosphatidyl serine;
Clove oil, and phosphatidyl serine;
Cassia oil, and phosphatidyl serine;
Cinnamon oil, and phosphatidyl serine;
an oil having a specific gravity from 0.90 to 0.95, and phosphatidyl serine;
Almond oil, and phosphatidyl serine;
Corn oil, and phosphatidyl serine;
Arachis oil, and phosphatidyl serine;
Cottonseed oil, and phosphatidyl serine;
Safflower oil, and phosphatidyl serine;
Maize oil, and phosphatidyl serine;
Linseed oil, and phosphatidyl serine;
Rapeseed oil, and phosphatidyl serine;
Soybean oil, and phosphatidyl serine;
Olive oil, and phosphatidyl serine;
Caraway oil, and phosphatidyl serine;
Rosemary oil, and phosphatidyl serine;
Peanut oil, and phosphatidyl serine;
Peppermint oil, and phosphatidyl serine;
Sunflower oil, and phosphatidyl serine;
Eucalyptus oil, and phosphatidyl serine;
Sesame oil, and phosphatidyl serine;
an oil having a specific gravity below 0.9, and phosphatidyl serine;
Mineral oil, and phosphatidyl serine;
Coriander oil, and phosphatidyl serine;
Lavender oil, and phosphatidyl serine;
Citronella oil, and phosphatidyl serine;
Juniper oil, and phosphatidyl serine;
Lemon oil, and phosphatidyl serine;
Orange oil, and phosphatidyl serine;
Clary sage oil, and phosphatidyl serine;
Nutmeg oil, and phosphatidyl serine; and,
Tea tree oil, and phosphatidyl serine.

In one embodiment, the presently useful compositions are self-emulsifying which, when exposed to an aqueous medium, form fine oil-in-water emulsions with little or no agitation. The property of self-emulsification permits such formulations to be administered in concentrated form, as for example in a soft gelatin or viscous paste. Additionally, emulsions may be prepared by combining a self-emulsifying pre-concentrate with an aqueous medium.

Examples of self-emulsifying systems include those in which an active component such as a prostaglandin and/or prostamide component is combined with mixtures of (i) medium-chain triglycerides and nonionic surfactants, (ii) vegetable oils and partial glycerides, such as polyglycolized glycerides or medium-chain mono- and diglycerides, or (iii) vegetable oils and nonionic surfactants such as polysorbate 80 or PEG-25 glyceryl trioleate.

In further examples of self-emulsifying formulations, a "microemulsion preconcentrate" of a prostaglandin and/or prostamide component can be formed by combining the prostaglandin and/or prostamide component with (I) a hydrophilic phase, (II) a lipophilic phase, and (III) a surfactant, as well as optional thickeners, antioxidants or other excipients.

In addition, suitable compositions may include an active such as prostaglandin and/or prostamide components in combination with a hydrophilic solvent phase and one or more surfactants, but not containing lipophilic solvents. Such prostaglandin and/or prostamide component-containing formulations may be stable, simple to prepare, and have good pharmacokinetic properties.

Except as otherwise noted elsewhere herein, the compositions of the present invention are administered topically. However, other modes of administration are possible such as systemic administration, for example, oral administration of a capsule or suspension, intramuscular, intraperitoneal, subcutaneous and intraarticular injection or infusion of a prostaglandin and/or prostamide component-containing composition. Topical administration includes ointments, drops, solutions, lacquers (pigmented nail polish or lacquer comprising a separate anti-fungal agent), suspensions or emulsions including a prostaglandin and/or prostamide component which may be administered using an applicator system which are well known in the art. Topical formulations, intended for topical administration to the affected tissue area or areas, may be prepared directly, or by combining a prostaglandin and/or prostamide component-containing concentrate with a diluent, for example, an aqueous diluent. Such topical formulations may include additional excipients as necessary, for example, to modify consistency of the rate of absorption of the prostaglandin and/or prostamide component.

In preparing the presently useful compositions, the components may be combined in any order with mixing or light agitation to ensure complete blending.

The compositions of the present invention may be administered in a sufficient amount, and for a sufficient time, as required to provide the desired therapeutic effect of improving nail health. The composition of the present invention may be administered concurrently with other therapeutics such as orally administered anti-fungal agents. The specific therapeutically effective dosage level may be dependent on a number of factors including the specific condition to be treated, the severity of the condition, the activity of the particular prostaglandin and/or prostamide component being employed, the specific prostaglandin and/or prostamide component-containing composition employed, the time and method of administration, the duration of treatment, and other factors which are well known in the medical arts.

The present invention is not to be limited in scope by the specific embodiments disclosed in the examples which are intended as illustrations of a few aspects of the invention and any embodiments that are functionally equivalent are within the scope of this invention.

Indeed, various modifications of the invention in addition to those shown and described herein will become apparent to those skilled in the relevant art and are intended to fall within the scope of the appended claims.

Each and every reference cited herein, whether a granted patent, patent application, or a journal/scientific publication, is incorporated herein by reference in its entirety for all purposes.

The invention claimed is:

1. A method of treating brittle nail syndrome in a human patient, the method comprising topically administering to a nail of the patient a composition comprising bimatoprost, wherein the composition is applied topically to the nail of the patient.

2. The method of claim 1, further comprising administering at least one of an anti-inflammatory agent, and immunomodulator; or a mixture thereof.

3. The method of claim 2, wherein the anti-inflammatory agent is ketorolac.

4. The method of claim 2, wherein the immunomodulator is cyclosporine A.

5. The method of claim 1, wherein the composition is in an oil-in-water emulsion.

6. The method of claim 5, wherein the emulsion comprises castor oil and a surfactant.

7. The method of claim 5, wherein the emulsion comprises at least one component selected from the group consisting of glycerin, polysorbate 80 and carbomer.

8. The method of claim 5, wherein the composition in an oil-in water emulsion further comprises 0.5%-1.5% w/w polysorbate 80, 0.5%-1.5% w/w glycerine, 0.5%-1.5% w/w castor oil, 0.05%-0.1% w/w carbomer 1342 and mannitol.

9. The method of claim 1, wherein the composition is administered at least once a day.

10. The method of claim 6, wherein the oil is selected from the group consisting of: Anise oil; Castor oil; Clove oil; Cassia oil; Cinnamon oil; oils having a specific gravity between 0.90 and 0.95; Almond oil; Corn oil; Arachis oil; Cottonseed oil; Safflower oil; Maize oil; Linseed oil; Rapeseed oil; Soybean oil; Olive oil; Caraway oil; Rosemary oil; Peanut oil; Peppermint oil; Sunflower oil; Eucalyptus oil; Sesame oil; an oil having a specific gravity below 0.9; Mineral oil; Coriander oil; Lavender oil; Citronella oil; Juniper oil; Lemon oil; Orange oil; Clary sage oil; Nutmeg oil; and, Tea tree oil and mixtures thereof.

11. The method of claim 5, wherein the oil-in-water emulsion further contains a surfactant selected from the group consisting of Polysorbate 80, carboxylated and ethoxylated alcohols, amine oxides, block polymers, fatty acids, ethoxylated alkyl phenols, ethoxylated fatty esters, glycerol esters, lanolin-based derivatives, lignin derivatives, methyl esters, mono- and tri-glycerides, polyethylene glycols, polymeric surfactants, propoxylated and ethoxylated fatty acids, alcohols, alkyl phenols, protein based surfactants, sucrose and glucose esters, and derivatives and mixtures thereof.

12. The method of claim 5, wherein the oil is present in a concentration selected from the group consisting of 1.25% w/v, 0.01%-w/v-10.0% w/v, 0.1% w/v-5.0% w/v, 0.1% w/v-4.0% w/v, 0.1% w/v-3.0% w/v, 0.1% w/v-2.0% w/v, 0.1% w/v-1.0% w/v, 0.1% w/v-0.9% w/v, 0.1% w/v-0.8% w/v, 0.1% w/v-0.7% w/v, 0.1% w/v-0.6% w/v, 0.1% w/v-0.5% w/v, 0.1% w/v-0.4% w/v, 0.1% w/v-0.3% w/v, 0.1% w/v-0.2% w/v, 0.09%-0.1% w/v, 0.08%-0.1% w/v, 0.07%-0.1% w/v, 0.06%-0.1% w/v, 0.05%-0.1% w/v, 0.04%-0.1% w/v, 0.03%-0.1% w/v, 0.02%-0.1% w/v, 0.01%-0.1% w/v, 0.01-0.09%, 0.01-0.08% 0.01-0.07% w/v, 0.01-0.06% w/v, 0.01-0.05% w/v, 0.01-0.04% w/v, 0.01-0.03% w/v, 0.01-0.02% w/v, 0.01-0.0125% w/v, and 0.05% w/v-5.0% w/v.

13. The method of claim 11, wherein the surfactant is present in a concentration selected from the group consisting of 1.0% w/v, 0.01%-w/v-10.0% w/v, 0.1% w/v-5.0% w/v, 0.1% w/v-4.0% w/v, 0.1% w/v-3.0% w/v, 0.1% w/v-2.0% w/v, 0.1% w/v-1.0% w/v, 0.1% w/v-0.9% w/v, 0.1% w/v-0.8% w/v, 0.1% w/v-0.7% w/v, 0.1% w/v-0.6% w/v, 0.1% w/v-0.5% w/v, 0.1% w/v-0.4% w/v, 0.1% w/v-0.3% w/v, 0.1% w/v-0.2% w/v, 0.09%-0.1% w/v, 0.08%-0.1% w/v, 0.07%-0.1% w/v, 0.06%-0.1% w/v, 0.05%-0.1% w/v, 0.04%-0.1% w/v, 0.03%-0.1% w/v, 0.02%-0.1% w/v, 0.01%-0.1% w/v, 0.01-0.09%, 0.01-0.08% 0.01-0.07% w/v, 0.01-0.06% w/v, 0.01-0.05% w/v, 0.01-0.04% w/v, 0.01-0.03% w/v, 0.01-0.02% w/v and 0.01-0.0125% w/v.

\* \* \* \* \*